(12) United States Patent
Peter

(10) Patent No.: US 9,365,650 B2
(45) Date of Patent: Jun. 14, 2016

(54) SINGLE CHAIN ANTIBODIES THAT SPECIFICALLY BIND TO THE ACTIVATED STATE OF THE PLATELET INTEGRIN RECEPTOR GP IIB/IIIA

(75) Inventor: Karlheinz Peter, Victoria (AU)

(73) Assignee: Baker IDI Heart and Diabetes Institute Holdings Limited, Melbourne, Victoria (AU)

( * ) Notice: Subject to any disclaimer, the term of this patent is extended or adjusted under 35 U.S.C. 154(b) by 2303 days.

(21) Appl. No.: 13/986,452

(22) Filed: Jan. 2, 2008

(65) Prior Publication Data

US 2014/0243502 A1 Aug. 28, 2014

Related U.S. Application Data

(63) Continuation-in-part of application No. PCT/AU2006/000943, filed on Jul. 5, 2006.

(30) Foreign Application Priority Data

Jul. 5, 2005 (AU) ................................ 2005903570
Oct. 6, 2005 (AU) ................................ 2005905522

(51) Int. Cl.

| C07K 16/28 | (2006.01) |
| A61K 39/395 | (2006.01) |
| A61K 47/48 | (2006.01) |
| A61K 49/16 | (2006.01) |
| A61K 49/18 | (2006.01) |
| A61K 51/10 | (2006.01) |
| A61K 49/04 | (2006.01) |
| C07K 14/81 | (2006.01) |
| A61K 39/00 | (2006.01) |

(52) U.S. Cl.
CPC ....... *C07K 16/2848* (2013.01); *A61K 47/48561* (2013.01); *A61K 49/04* (2013.01); *A61K 49/16* (2013.01); *A61K 49/1818* (2013.01); *A61K 51/1027* (2013.01); *C07K 14/811* (2013.01); *A61K 2039/505* (2013.01); *C07K 2317/34* (2013.01); *C07K 2317/622* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| 4,783,330 A | 11/1988 | Furie et al. |
| 5,026,537 A | 6/1991 | Daddona et al. |
| 5,053,453 A * | 10/1991 | Ku ................................ 525/54.1 |
| 5,114,842 A | 5/1992 | Plow et al. |
| 5,227,469 A | 7/1993 | Lazarus et al. |
| 5,242,810 A | 9/1993 | Maraganore et al. |
| 5,284,751 A | 2/1994 | Frelinger, III et al. |
| 5,334,369 A | 8/1994 | Halushka et al. |
| 5,470,738 A | 11/1995 | Frelinger, III et al. |
| 5,493,007 A | 2/1996 | Burnier et al. |
| 5,618,843 A | 4/1997 | Fisher et al. |
| 5,661,001 A | 8/1997 | Grossenbacher et al. |
| 5,736,339 A | 4/1998 | Scarborough et al. |
| 5,770,198 A * | 6/1998 | Coller et al. ............... 424/153.1 |
| 6,022,854 A | 2/2000 | Shuman |
| 6,056,958 A | 5/2000 | Mousa |
| 6,083,481 A | 7/2000 | Dean et al. |
| 6,159,443 A | 12/2000 | Hallahan |
| 6,230,713 B1 | 5/2001 | Dalesandro et al. |
| 6,472,405 B1 | 10/2002 | Fisher et al. |
| 7,049,140 B1 | 5/2006 | Hallahan |
| 2007/0218067 A1 | 9/2007 | Buttner et al |

FOREIGN PATENT DOCUMENTS

| EP | 1300419 | * | 4/2003 |
| EP | 1300419 A1 | | 4/2003 |
| EP | 1719529 A1 | | 11/2006 |
| WO | WO-90/04634 A1 | | 5/1990 |
| WO | WO-03/031476 A1 | | 4/2003 |

OTHER PUBLICATIONS von zur Muhlen et al., A Single Chain Antibody Directed Against Activated Platelets Allows Targeted Magnetic Resonance Imaging of Human Thrombi at Clinically Relevant Field Strengths, Poster 2005.*
von zur Muhlen et al., Activated Platelets can be Imaged by Activation Specific Glycoprotein IIb/IIIa Antibodies Conjugated to Iron Oxide Microparticles in an ex vivo Magnetic Resonance imaging mouse model, pp. 1-2, 2006 Abstract . . . .*
Stoll et al,. Targeting of the Direct FXa Inhibitor TAP via the Fusion of a Single Chain Antibody Directed Against a LIBS Epitope on GPIIb/IIA Provides Effective Anticoagulation Without Bleeding Time Prolongation, Journal of Thrombosis and Haemostasis Abstract No. OR338, 2005).*
Schwarz et al., Journal of Pharmacology and Experimental Therapeutics (JPET) 308:1002-1011, 2004.*
Armstrong, "Unsticking Platelets: The Role of Glycoprotein IIb/IIIa Receptor Blockade," *CMAJ* 161(11):1423-1424 (1999).
Chamorro et al., Cerebrovascular Diseases 17(Supp13): 1-38 (2004).
Breitling et al., "Recombinant Antibodies," Frank Breitling and Stefan Dübel—Heidelberg; Berlin: Spektrum, Akad. Verl., 1997.
Chung et al., "Integrin alphaIIbbeta3-Specific Synthetic Human Monoclonal Antibodies and HCDR3 Peptides that Potently Inhibit Platelet Aggregation," FASEB J. 18(2):(23 pages) (2003).
Di Nisio et al., "Direct Thrombin Inhibitors," N. Engl. J. Med. 353(10):1028-1040 (2005).

(Continued)

*Primary Examiner* — Phillip Gambel
(74) *Attorney, Agent, or Firm* — Clark & Elbing LLP

(57) ABSTRACT

The present invention provides an anticoagulant agent including a first element capable of inhibiting coagulation and a second element capable of targeting an activated platelet wherein upon administration of the agent to a subject the second element directs the first element to the activated platelet. Also provided is a probe for detecting a blood vessel abnormality including (a) a binding element capable of targeting an activated platelet and (b) a label. Applicant has shown that agents and probes directed to activated platelets are useful in the diagnosis and therapy of coagulation disorders.

17 Claims, 17 Drawing Sheets

(56) References Cited

OTHER PUBLICATIONS

Exploring New Antiplatelet Strategies and Imaging Techniques for Improved Acute and Long-Term Management of Stroke Patients. Cerebrovascular Diseases. Bogousslaysky, Davalos, Diez-Tejedor, and Hacke. (5 pages) (2003).
Farrehi et al., "Regulation of Arterial Thrombolysis by Plasminogen Activator Inhibitor-1 in Mice," Circulation 97(10):1002-1008 (1998).
Hagemeyer et al., "Fibrin-Targeted Direct Factor Xa Inhibition: Construction and Characterization of a Recombinant Factor Xa Inhibitor Composed of an Anti-Fibrin Single-Chain Antibody and Tick Anticoagulant Peptide," Thromb Haemost 92(1):47-53 (2004).
Huang et al., "Platelet Glycoprotein IIb/IIIa Inhibition and Its Clinical Use," Curr. Med. Chem. Cardiovasc. Hematol. Agents. 2(3):187-196 (2004).
Jennings et al., "The Pharmacodynamics of Parenteral Glycoprotein IIb/IIIa Inhibitors," J Interv Cardiol 15(1):45-60 (2002).
Kipriyanov et al., "High Level Production of Soluble Single Chain Antibodies in Small-Scale *Escherichia coli* Cultures," J Immunol Methods. 200:69-77 (1997).
Knapp et al., "Hirudisins. Hirudin-derived thrombin inhibitors with disintegrin activity," J Biol Chem. 267(34):24230-24234 (1992).
Mehta et al., "Update on Anticoagulant Medications for the Interventional Radiologist," J. Vasc. Interv. Radiol. 17(4):597-612 (2006).
Neeper et al., "Characterization of Recombinant Tick Anticoagulant Peptide. A Highly Selective Inhibitor of Blood Coagulation Factor Xa," J. Biol. Chem. 265(29):17746-17752 (1990).
NCBI Blast for Accession No. M60480. Retrieved on Aug. 28, 2007 (1 page).
Roque et al., "Mouse Model of Femoral Artery Denudation Injury Associated with the Rapid Accumulation of Adhesion Molecules on the Luminal Surface and Recruitment of Neutrophils," Arterioscler. Thromb. Vasc. Biol. 20:335-342 (2000).
Schwarz et al., "Conformation-Specific Blockade of the Integrin GPIIb/IIIa: a novel antiplatelet strategy that selectively targets activated platelets," Circ Res. 99(1):25-33 (2006).
Schwarz et al., "Single-Chain Antibodies for the Conformation-Specific Blockade of Activated Platelet Integrin alphaIIbbeta3 Designed by Subtractive Selection from Naïve Human Phage Libraries," FASEB J. 18(14): (29 pages) (2004).
Schwarz et al., "Reversibility Versus Persistence of GPIIb/IIIa Blocker-Induced Conformational Change of GPIIb/IIIa ( αIIbβ3 , CD41/CD61)," J Pharmacol Exp Ther 308(3):1002-1011 (2004).
Stoll et al., "Targeting of the Direct FXa Inhibitor TAP via the Fusion of a Single-Chain Antibody Directed Against a LIBS Epitope on GPIIb/IIIa Provides Effective Anticoagulation Without Bleeding Time Prolongation," J Thromb Haemost. 3 (Suppl 1): Abstract No. OR338 (2 pages) (2005).
Topol et al., "Comparison of Two Platelet Glycoprotein IIb/IIIa Inhibitors, Tirofiban and Abciximab, for the prevention of Ischemic Events with Percutaneous Coronary Revascularization," N. Engl. J. Med. 344(25):1888-1894 (2001).
Von zur Muhlen et al., "A Single-Chain Antibody Directed Against Activated Platelets Allows Targeted Magnetic Resonance Imaging of Human Thrombi at Clinically Relevant Field Strengths," Circulation 112 (Abstract 1092) (2005).
Von zur Muhlen et al., "A Single-Chain Antibody Directed Against Activated Platelets Allows Targeted Magnetic Resonance Imaging of Human Thrombi at Clinically Relevant Field Strengths," Poster (1 page) (2005).
Von zur Muhlen et al., "Activated Platelets can be Imaged by Activation-Specific Glycoprotein IIb/IIIa Antibodies Conjugated to Iron Oxide Microparticles in an ex vivo Magnetic resonance imaging mouse model. " (Abstract) (2 pages) (2006).
Wang et al., Prevention of Platelet Glycoprotein IIb/IIIa Activation by a Novel Tyrosine Kinase Inhibitor 3,4-Methylenedioxy-β-Nitrostyrene, Mol Pharmacol. (56 pages) (2006).
Waxman et al., "Tick Anticoagulant Peptide (TAP) is a Novel Inhibitor of Blood Coagulation Factor Xa" Science. 248(4955): (4 pages) (1990).
Weitz et al., "Direct Thrombin Inhibitors in Acute Coronary Syndromes: Present and Future," Circulation 105:1004-1011 (2002).
Welschof et al., "Amino Acid Sequence Based PCR Primers for Amplification of Rearranged Human Heavy and Light Chain Immunoglobulin Variable Region Genes," J Immunol Methods. 179(2): 203-214 (1995).
The Journal of Pharmacology and Experimental Therapeutics Instructions to Authors revised May 2, 2013 (5 pages).
"Instructions to Authors: The Journal of Pharmacology and Experimental Therapeutics," <http://web.archive.org/web/20090302062742/http://jpet.aspetjournals.org/misc/ifora.shtml> retrieved on Jun. 19, 2013 (4 pages).
Anderluh et al., "Toward a novel class of antithrombotic compounds with dual function. Discovery of 1,4-benzoxazin-3(4H)-one derivatives possessing thrombin inhibitory and fibrinogen receptor antagonistic activities," J Med Chem. 48(9):3110-3 (2005).
Applegate et al., "Vascular closure devices in patients treated with anticoagulation and IIb/IIIa receptor inhibitors during percutaneous revascularization," J Am Coll Cardiol. 40(1):78-83 (2002).
Bates et al., "Imaging characteristics of a novel technetium Tc 99m-labeled platelet glycoprotein IIb/IIIa receptor antagonist in patients with acute deep vein thrombosis or a history of deep vein thrombosis," Arch Intern Med. 163(4):452-6 (2003).
Blomley et al., "Microbubble contrast agents: a new era in ultrasound," BMJ. 322(7296):1222-5 (2001).
Bogousslaysky et al., "Exploring New Antiplatelet Strategies and Imaging Techniques for Improved Acute and Long-Term Management of Stroke Patients," Cerebrovascular Diseases, Sanofi-Synthelabo and Bristol-Myers Squibb Satellite and Educational Symposia at the 12th European Stroke Conference, May 21-22, 2003, Valencia, Spain (43 pages).
Chen et al., "Fusion proteins comprising annexin V and Kunitz protease inhibitors are highly potent thrombogenic site-directed anticoagulants," Blood. 105(10):3902-9 (2005).
Davies et al., "Molecular and metabolic imaging of atherosclerosis," J Nucl Med. 45(11):1898-907 (2004).
Kunitada et al., "Factor Xa Inhibitors," Current Pharmaceutical Design 2:531-542 (1996).
Levi, "Cell surface-targeted anticoagulation in systemic infection and inflammation," Blood. 104(5):1231-2 (2004).
Lister-James et al., "Thrombus imaging with a technetium-99m-labeled activated platelet receptor-binding peptide," J Nucl Med. 37(5):775-81 (1996).
Mitchel et al., "Identification of coronary thrombus with a IIb/IIIa platelet inhibitor radiopharmaceutical, technetium-99m DMP-444: A canine model," Circulation. 101(14):1643-6 (2000).
Palabrica et al., "Thrombus imaging in a primate model with antibodies specific for an external membrane protein of activated platelets," Proc Natl Acad Sci U.S.A. 86(3):1036-40 (1989).
Peter et al., "Construction and functional evaluation of a single-chain antibody fusion protein with fibrin targeting and thrombin inhibition after activation by factor Xa," Circulation 101(10):1158-64 (2000).
Taillefer et al., "Comparison of early and delayed scintigraphy with 99mTc-apcitide and correlation with contrast-enhanced venography in detection of acute deep vein thrombosis," J Nucl Med. 40(12):2029-35 (1999).
Thakur et al., "Imaging vascular thrombosis with 99mTc-labeled fibrin alpha-chain peptide," J Nucl Med. 41(1):161-8 (2000).
Verstraete, "New developments in antiplatelet and antithrombotic therapy," Eur Heart J. 16 Suppl L:16-23 (1995).
Zhang et al., "Functional properties of a recombinant chimeric plasminogen activator with platelet-targeted fibrinolytic and anticoagulant potential," Mol Genet Metab. 82(4):304-11 (2004).

* cited by examiner

Figure 1

5'-TGA CCA TGA TTA CGA ATT TCT GAA GAA GGA GAT ATA CAT$^{40}$ATG AAA TAC CTA TTG CCT ACG GCA GCC GCT GGC TTG CTG CTG CTG GCA GCT CAG CCG GCC ATG GCG$^{106}$GTG CAG CTG CAG CAG TCT GGG GGA GGC TTA GTG AAG CCT GGA GGG TCC CTG AAA CTC TCC TGC GCA GCC TCT GGA TTC ACT TTC AGT AGC TAT ATC ATG TCT$^{208}$TGG GTT CGC CAG ACT CCG GAG AAG AGG CTG GAG TGG GTC GCA ACC ATT AGA AGT GGT GGT GAT AAC ACC TAC TAT CCA GAC AGT GTG AAG GGT CGA TTC ACC ATC TCC AGA GAC AAT GCC AAG AAC AAG TTG TAC CTG CAA ATG AGC AGT CTG AGG TCT GAG GAC ACG GCC TTG TAT TAC TGT GCA ATC TAC TAT GGT AAC TAC GGG GGG CTT GCT TAC TGG GGC CAA GGG ACT CTG GTC ACT GTC TCT GCA GCC AAA ACG ACA CCC AAG CTT$^{481}$GAA GAA GGT GAA TTT TCA GAA GCA CGC$^{508}$GTA GAT ATC TTG ATG ACC CAA TCT CCA GCC TCC CTA TCT GCA TCT GTG GGA GAA ACT GTC ACC ATC ACA TGT CGA GCA AGT GGG AAT ATT CAC AAT TAT TTA GCA TGG TAT CAG CAG AAA CAG GGA AAA TCT CCT CAG CTC CTG GTC TAT AAT GCA AAA ACC TTA GCA GAT GGT GTG CCA TCA AGG TTC AGT GGC AGT GGA TCA GGA ACA CAA TAT TCT CTC AAG ATC AAC AGC CTG CAG CCT GAA GAT TTT GGG AGT TAT TAC TGT CAA CAT TTT TGG AGT ACT CCG TAC ACG TTC GGA GGG GGG ACC AAG CTG GAA ATA AAA CGG GCT GAT GCT GCG GCC GCT GGA TCC$^{859}$TAC AAC CGT CTG TGC ATC AAA CCG CGT GAC TGG ATC GAC GAA TGC GAC TCC AAC GAA GGT GGT GAA CGT GCT TAC TTC CGT AAC GGT AAA GGT GGT TGC GAC TCC TTC TGG ATC TGC CCG GAA GAC ACC GGT GCT GAC TAC TAC TCC TCC TAC CGT GAC TGC TTC AAC GCT TGC ATC$^{1039}$GGT GGA GGC TCA GGA GAT CTA AAC TCA$^{1066}$CAT CAC CAT CAC CAT CAC TAA- 3'

Figure 10
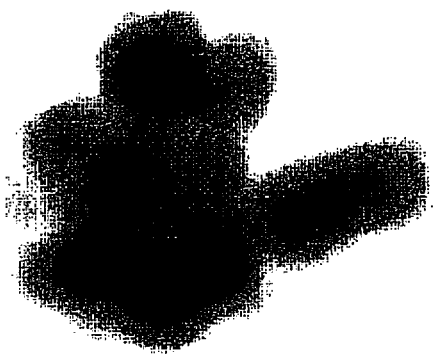

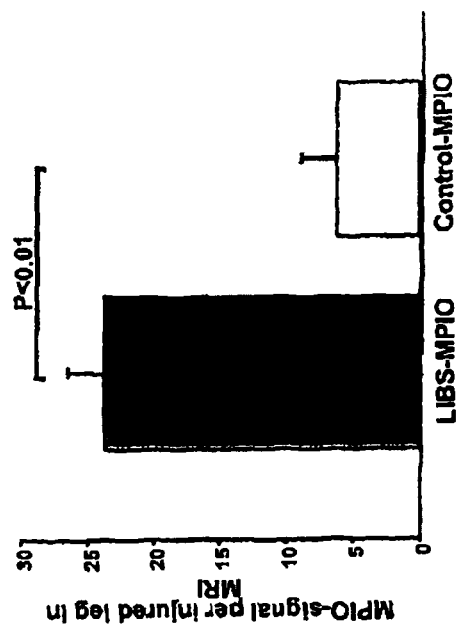
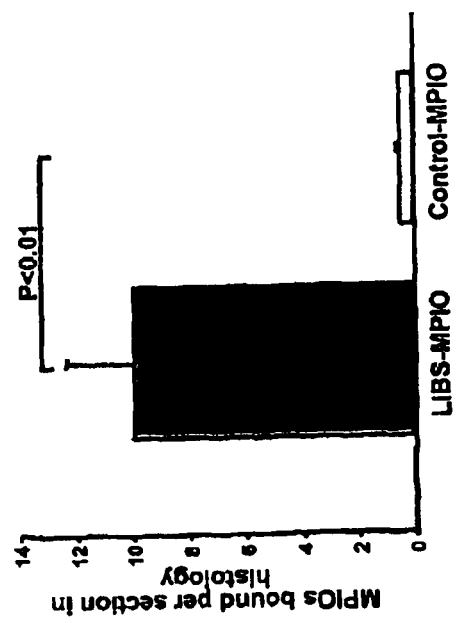
FIG. 15D

SEQUENCE LISTING

```
<160> NUMBER OF SEQ ID NOS: 12

<210> SEQ ID NO 1
<211> LENGTH: 1086
<212> TYPE: DNA
<213> ORGANISM: Artificial Sequence
<220> FEATURE:
<223> OTHER INFORMATION: synthetic

<400> SEQUENCE: 1
tgaccatgat tacgaatttc tgaagaagga gatatacata tgaaatacct attgcctacg      60
gcagccgctg gcttgctgct gctggcagct cagccggcca tggcggtgca gctgcagcag     120
tctgggggag gcttagtgaa gcctggaggg tccctgaaac tctcctgcgc agcctctgga     180
ttcactttca gtagctatat catgtcttgg gttcgccaga ctccggagaa gaggctggag     240
tgggtcgcaa ccattagaag tggtggtgat aacacctact atccagacag tgtgaagggt     300
cgattcacca tctccagaga caatgccaag aacaagttgt acctgcaaat gagcagtctg     360
aggtctgagg acacggcctt gtattactgt gcaatctact atggtaacta cgggggctt      420 gcttactggg gccaagggac tctggtcact gtctctgcag ccaaaacgac acccaagctt     480
gaagaaggtg aatttcaga agcacgcgta gatatcttga tgacccaatc tccagcctcc     540
ctatctgcat ctgtgggaga aactgtcacc atcacatgtc gagcaagtgg gaatattcac     600
aattatttag catggtatca gcagaaacag ggaaaatctc ctcagctcct ggtctataat     660
gcaaaaacct tagcagatgg tgtgccatca aggttcagtg gcagtggatc aggaacacaa     720
tattctctca agatcaacag cctgcagcct gaagattttg ggagttatta ctgtcaacat     780
ttttggagta ctccgtacac gttcggaggg gggaccaagc tggaaataaa acgggctgat     840
gctgcggccg ctggatccta caaccgtctg tgcatcaaac cgcgtgactg gatcgacgaa     900
tgcgactcca acgaaggtgg tgaacgtgct tacttccgta acggtaaagg tggttgcgac     960
tccttctgga tctgcccgga agaccacacc ggtgctgact actactcctc ctaccgtgac    1020
```

```
tgcttcaacg cttgcatcgg tggaggctca ggagatctaa actcacatca ccatcaccat   1080
cactaa                                                              1086
```

<210> SEQ ID NO 2
<211> LENGTH: 359
<212> TYPE: PRT
<213> ORGANISM: Artificial Sequence
<220> FEATURE:
<223> OTHER INFORMATION: synthetic

<400> SEQUENCE: 2

```
Pro Leu Arg Ile Ser Glu Glu Gly Asp Ile His Met Lys Tyr Leu Leu
1               5                   10                  15

Pro Thr Ala Ala Ala Gly Leu Leu Leu Ala Ala Gln Pro Ala Met
            20                  25                  30

Ala Val Gln Leu Gln Gln Ser Gly Gly Gly Leu Val Lys Pro Gly Gly
        35                  40                  45

Ser Leu Lys Leu Ser Cys Ala Ala Ser Gly Phe Thr Phe Ser Ser Tyr
    50                  55                  60

Ile Met Ser Trp Val Arg Gln Thr Pro Glu Lys Arg Leu Glu Trp Val
65                  70                  75                  80

Ala Thr Ile Arg Ser Gly Gly Asp Asn Thr Tyr Tyr Pro Asp Ser Val
                85                  90                  95

Lys Gly Arg Phe Thr Ile Ser Arg Asp Asn Ala Lys Asn Lys Leu Tyr
            100                 105                 110

Leu Gln Met Ser Ser Leu Arg Ser Glu Asp Thr Ala Leu Tyr Tyr Cys
        115                 120                 125

Ala Ile Tyr Tyr Gly Asn Tyr Gly Gly Leu Ala Tyr Trp Gly Gln Gly
    130                 135                 140

Thr Leu Val Thr Val Ser Ala Ala Lys Thr Thr Pro Lys Leu Glu Glu
145                 150                 155                 160

Gly Glu Phe Ser Glu Ala Arg Val Asp Ile Leu Met Thr Gln Ser Pro
                165                 170                 175

Ala Ser Leu Ser Ala Ser Val Gly Glu Thr Val Thr Ile Thr Cys Arg
            180                 185                 190

Ala Ser Gly Asn Ile His Asn Tyr Leu Ala Trp Tyr Gln Gln Lys Gln
        195                 200                 205

Gly Lys Ser Pro Gln Leu Leu Val Tyr Asn Ala Lys Thr Leu Ala Asp
    210                 215                 220

Gly Val Pro Ser Arg Phe Ser Gly Ser Gly Ser Gly Thr Gln Tyr Ser
225                 230                 235                 240

Leu Lys Ile Asn Ser Leu Gln Pro Glu Asp Phe Gly Ser Tyr Tyr Cys
                245                 250                 255

Gln His Phe Trp Ser Thr Pro Tyr Thr Phe Gly Gly Gly Thr Lys Leu
            260                 265                 270

Glu Ile Lys Arg Ala Asp Ala Ala Ala Gly Ser Tyr Asn Arg Leu
        275                 280                 285

Cys Ile Lys Pro Arg Asp Trp Ile Asp Glu Cys Asp Ser Asn Glu Gly
    290                 295                 300

Gly Glu Arg Ala Tyr Phe Arg Asn Gly Lys Gly Cys Asp Ser Phe
305                 310                 315                 320

Trp Ile Cys Pro Glu Asp His Thr Gly Ala Asp Tyr Tyr Ser Ser Tyr
                325                 330                 335

Arg Asp Cys Phe Asn Ala Cys Ile Gly Gly Ser Gly Asp Leu Asn
            340                 345                 350
```

Ser His His His His His His
    355

<210> SEQ ID NO 3
<211> LENGTH: 30
<212> TYPE: DNA
<213> ORGANISM: Artificial Sequence
<220> FEATURE:
<223> OTHER INFORMATION: amplification primer

<400> SEQUENCE: 3
ccggccatgg cgcaggtgca gctgcagcag                              30

<210> SEQ ID NO 4
<211> LENGTH: 38
<212> TYPE: DNA
<213> ORGANISM: Artificial Sequence
<220> FEATURE:
<223> OTHER INFORMATION: amplification primer

<400> SEQUENCE: 4 ccagggggcca gtggatagac aagcttgggt gtcgtttt                    38

<210> SEQ ID NO 5
<211> LENGTH: 43
<212> TYPE: DNA
<213> ORGANISM: Artificial Sequence
<220> FEATURE:
<223> OTHER INFORMATION: amplification primer

<400> SEQUENCE: 5
aattttcaga agcacgcgta gatatcktgm tsacccaawc tcc               43

<210> SEQ ID NO 6
<211> LENGTH: 30
<212> TYPE: DNA
<213> ORGANISM: Artificial Sequence
<220> FEATURE:
<223> OTHER INFORMATION: amplification primer

<400> SEQUENCE: 6
gaagatggat ccagcggccg cagcatcagc                              30

<210> SEQ ID NO 7
<211> LENGTH: 10
<212> TYPE: PRT
<213> ORGANISM: Artificial Sequence
<220> FEATURE:
<223> OTHER INFORMATION: synthetic

<400> SEQUENCE: 7

Gly Phe Thr Phe Ser Ser Tyr Ile Met Ser
1               5                   10

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Thr Ile Arg Ser Gly Gly Asp Asn Thr Tyr Tyr Pro Asp Ser Val Lys
1               5                   10                  15

Gly

```
<210> SEQ ID NO 9
<211> LENGTH: 10
<212> TYPE: PRT
<213> ORGANISM: Artificial Sequence
<220> FEATURE:
<223> OTHER INFORMATION: synthetic

<400> SEQUENCE: 9

Tyr Tyr Gly Asn Tyr Gly Gly Leu Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic

<400> SEQUENCE: 10

Arg Ala Ser Gly Asn Ile His Asn Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic

<400> SEQUENCE: 11

Asn Ala Lys Thr Leu Ala Asp
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic

<400> SEQUENCE: 12

Gln His Phe Trp Ser Thr Pro Tyr Thr
1               5
```

SINGLE CHAIN ANTIBODIES THAT SPECIFICALLY BIND TO THE ACTIVATED STATE OF THE PLATELET INTEGRIN RECEPTOR GP IIB/IIIA

This application is a continuation-in-part application of International Application No. PCT/AU2006/000943, filed 5 Jul. 2006, which claims benefit of Australian Patent Application Nos. AU 2005903570, filed 5 Jul. 2005, and AU 2005905522, filed 6 Oct. 2005, hereby incorporated by reference.

FIELD OF THE INVENTION

The present invention relates to the field of haematology and particularly the sub-specialty of haemostasis. More specifically, the present invention relates to 1) agents that inhibit coagulation in mammalian blood, and uses for these agents in the treatment and prevention of diseases such as stroke, myocardial infarction, and deep vein thrombosis and 2) probes that allow diagnosis and identification of activated platelets in clinical settings such as thrombosis, thrombotic emboli as well as unstable plaques.

BACKGROUND TO THE INVENTION

The ability of the body to control the flow of blood following vascular injury is paramount to continued survival. The process of blood clotting and then the subsequent dissolution of the clot, following repair of the injured tissue, is termed hemostasis. Hemostasis is composed of a number of events that occur in a set order following the loss of vascular integrity:

The initial phase of the process is vascular constriction. This limits the flow of blood to the area of injury. Next, platelets become activated by thrombin and aggregate at the site of injury, forming a temporary, loose platelet plug. The protein fibrinogen is primarily responsible for stimulating platelet clumping. Platelets clump by binding to collagen that becomes exposed following rupture of the endothelial lining of vessels. Upon activation, platelets release adenosine-5'-diphosphate, ADP and TXA2 (which activate additional platelets), serotonin, phospholipids, lipoproteins, and other proteins important for the coagulation cascade. In addition to induced secretion, activated platelets change their shape to accommodate the formation of the plug.

To insure stability of the initially loose platelet plug, a fibrin mesh (also called the clot) forms and entraps the plug. Finally, the clot must be dissolved in order for normal blood flow to resume following tissue repair. The dissolution of the clot occurs through the action of plasmin.

Two pathways lead to the formation of a fibrin clot: the intrinsic and extrinsic pathway. Although they are initiated by distinct mechanisms, the two converge on a common pathway that leads to clot formation. The formation of a red thrombus or a clot in response to an abnormal vessel wall in the absence of tissue injury is the result of the intrinsic pathway. Fibrin clot formation in response to tissue injury is the result of the extrinsic pathway. Both pathways are complex and involve numerous different proteins termed clotting factors
Platelet Activation and Von Willebrand Factor (vWF).

In order for hemostasis to occur, platelets must adhere to exposed collagen, release the contents of their granules, and aggregate. The adhesion of platelets to the collagen exposed on endothelial cell surfaces is mediated by von Willebrand factor (vWF). The function of vWF is to act as a bridge between a specific glycoprotein on the surface of platelets (GPIb/IX) and collagen fibrils. In addition to its role as a bridge between platelets and exposed collagen on endothelial surfaces, vWF binds to and stabilizes coagulation factor VIII. Binding of factor VIII by vWF is required for normal survival of factor VIII in the circulation.

Von Willebrand factor is a complex multimeric glycoprotein that is produced by and stored in the platelets. It is also synthesized by megakaryocytes and found associated with subendothelial connective tissue. The initial activation of platelets is induced by thrombin binding to specific receptors on the surface of platelets, thereby initiating a signal transduction cascade. The thrombin receptor is coupled to a G-protein that, in turn, activates phospholipase C-γ (PLC-γ). PLC-γ hydrolyzes phosphatidylinositol-4,5-bisphosphate (PIP2) leading to the formation of inositol trisphosphate (IP3) and diacylglycerol (DAG). IP3 induces the release of intracellular Ca2+ stores, and DAG activates protein kinase C (PKC).

The collagen to which platelets adhere as well as the release of intracellular Ca2+ leads to the activation of phospholipase A2 (PLA2), which then hydrolyzes membrane phospholipids, leading to liberation of arachidonic acid. The arachidonic acid release leads to an increase in the production and subsequent release of thromboxane A2 (TXA2). This is another platelet activator that functions through the PLC-γ pathway. Another enzyme activated by the released intracellular Ca2+ stores is myosin light chain kinase (MLCK). Activated MLCK phosphorylates the light chain of myosin which then interacts with actin, resulting in altered platelet morphology and motility.

One of the many effects of PKC is the phosphorylation and activation of a specific 47,000-Dalton platelet protein. This activated protein induces the release of platelet granule contents; one of which is ADP. ADP further stimulates platelets increasing the overall activation cascade; it also modifies the platelet membrane in such a way as to allow fibrinogen to adhere to the platelet surface, resulting in fibrinogen-induced platelet aggregation.

Activation of platelets is required for their consequent aggregation to a platelet plug. However, equally significant is the role of activated platelet surface phospholipids in the activation of the coagulation cascade.

The intrinsic clotting cascade is initiated when contact is made between blood and exposed endothelial cell surfaces. The extrinsic and intrinsic pathways converge at the point where factor X is activated to factor Xa. Factor Xa has a role in the further activation of factor VII to VIIa. Active factor Xa also hydrolyzes and activates prothrombin to thrombin. Thrombin can then activate factors XI, VIII and V furthering the cascade. Ultimately the role of thrombin is to convert fribrinogen to fibrin and to activate factor XIII to XIIIa. Factor XIIIa (also termed transglutaminase) cross-links fibrin polymers solidifying the clot.

The intrinsic pathway requires the clotting factors VIII, IX, X, XI, and XII. Also required are the proteins prekallikrein and high-molecular-weight kininogen, as well as calcium ions and phospholipids secreted from platelets. Each of these pathway constituents leads to the conversion of factor X (inactive) to factor Xa (active). Initiation of the intrinsic pathway occurs when prekallikrein, high-molecular-weight kininogen, factor XI and factor XII are exposed to a negatively charged surface. This is termed the contact phase. Exposure of collagen to a vessel surface is the primary stimulus for the contact phase.

The assemblage of contact phase components results in conversion of prekallikrein to kallikrein, which in turn activates factor XII to factor XIIa. Factor XIIa can then hydrolyze more prekallikrein to kallikrein, establishing a reciprocal activation cascade. Factor XIIa also activates factor XI to factor XIa and leads to the release of bradykinin, a potent vasodilator, from high-molecular-weight kininogen.

In the presence of Ca2+, factor XIa activates factor IX to factor IXa. Factor IX is a proenzyme that contains vitamin K-dependent γ-carboxyglutamate (gla) residues, whose serine protease activity is activated following Ca2+ binding to these gla residues. Several of the serine proteases of the cascade (II, VII, IX, and X) are gla-containing proenzymes. Active factor IXa cleaves factor X at an internal arg-ile bond leading to its activation to factor Xa.

The activation of factor Xa requires assemblage of the tenase complex (Ca2+ and factors VIIIa, IXa and X) on the surface of activated platelets. One of the responses of platelets to activation is the presentation of phosphatidylserine and phosphatidylinositol on their surfaces. The exposure of these phospholipids allows the tenase complex to form. The role of factor VIII in this process is to act as a receptor, in the form of factor VIIIa, for factors IXa and X. Factor VIIIa is termed a cofactor in the clotting cascade. The activation of factor VIII to factor VIIIa (the actual receptor) occurs in the presence of minute quantities of thrombin. As the concentration of thrombin increases, factor VIIIa is ultimately cleaved by thrombin and inactivated. This dual action of thrombin, upon factor VIII, acts to limit the extent of tenase complex formation and thus the extent of the coagulation cascade.

As discussed supra activated factor Xa is the site at which the intrinsic and extrinsic coagulation cascades converge. The extrinsic pathway is initiated at the site of injury in response to the release of tissue factor (factor III). Tissue factor is a cofactor in the factor Vila-catalyzed activation of factor X. Factor Vila, a gla residue containing serine protease, cleaves factor X to factor Xa in a manner identical to that of factor IXa of the intrinsic pathway. The activation of factor VII occurs through the action of thrombin or factor Xa. The ability of factor Xa to activate factor VII creates a link between the intrinsic and extrinsic pathways. An additional link between the two pathways exists through the ability of tissue factor and factor Vila to activate factor IX. While there is some uncertainty it appears the formation of complex between factor Vila and tissue factor is believed to be a principal step in the overall clotting cascade. A major mechanism for the inhibition of the extrinsic pathway occurs at the tissue factor-factor VIIa-Ca2+-Xa complex. The protein, lipoprotein-associated coagulation inhibitor, LACI specifically binds to this complex. LACI is also referred to as extrinsic pathway inhibitor, EPI or tissue factor pathway inhibitor, TFPI and was formerly named anticonvertin. LACI is composed of 3 tandem protease inhibitor domains. Domain 1 binds to factor Xa and domain 2 binds to factor Vila only in the presence of factor Xa Activation of Prothrombin to Thrombin The common point in both extrinsic and intrinsic pathways is the activation of factor X to factor Xa. Factor Xa activates prothrombin (factor II) to thrombin (factor IIa). Thrombin, in turn, converts fibrinogen to fibrin. The activation of thrombin occurs on the surface of activated platelets and requires formation of a prothrombinase complex. This complex is composed of the platelet phospholipids, phosphatidylinositol and phosphatidylserine, Ca2+, factors Va and Xa, and prothrombin. Factor V is a cofactor in the formation of the prothrombinase complex, similar to the role of factor VIII in tenase complex formation. Like factor VIII activation, factor V is activated to factor Va by means of minute amounts and is inactivated by increased levels of thrombin. Factor Va binds to specific receptors on the surfaces of activated platelets and forms a complex with prothrombin and factor Xa.

Prothrombin is a 72,000-Dalton, single-chain protein containing ten gla residues in its N-terminal region. Within the prothrombinase complex, prothrombin is cleaved at 2 sites by factor Xa. This cleavage generates a 2-chain active thrombin molecule containing an A and a B chain which are held together by a single disulfide bond.

In addition to its role in activation of fibrin clot formation, thrombin plays an important regulatory role in coagulation. Thrombin combines with thrombomodulin present on endothelial cell surfaces forming a complex that converts protein C to protein Ca. The cofactor protein S and protein Ca degrade factors Va and VIIIa, thereby limiting the activity of these two factors in the coagulation cascade.

Thrombin also binds to and leads to the release of G-protein-coupled protease activated receptors (PARs), specifically PAR-1, -3 and -4. The release of these proteins leads to the activation of numerous signaling cascades that in turn increase release of the interleukins, ILs, IL-1 and IL-6, increases secretion of intercellular adhesion molecule-1 (ICAM-1) and vascular cell adhesion molecule-1 (VCAM-1). The thrombin-induced signaling also leads to increased platelet activation and leukocyte adhesion. Thrombin also activates thrombin-activatable fibrinolysis inhibitor (TAFI) thus modulating fibrinolysis (degradation of fibrin clots). TAFI is also known as carboxypeptidase U (CPU) whose activity leads to removal of C-terminal lysines from partially degraded fibrin. This leads to an impairment of plasminogen activation, thereby reducing the rate of fibrin clot dissolution (i.e. fibrinolysis).

Control of Thrombin Levels

The inability of the body to control the circulating level of active thrombin would lead to dire consequences. There are two principal mechanisms by which thrombin activity is regulated. The predominant form of thrombin in the circulation is the inactive prothrombin, whose activation requires the pathways of proenzyme activation described above for the coagulation cascade. At each step in the cascade, feedback mechanisms regulate the balance between active and inactive enzymes.

The activation of thrombin is also regulated by four specific thrombin inhibitors. Antithrombin III is the most important since it can also inhibit the activities of factors IXa, Xa, XIa and XIIa. The activity of antithrombin III is potentiated in the presence of heparin by the following means: heparin binds to a specific site on antithrombin III, producing an altered conformation of the protein, and the new conformation has a higher affinity for thrombin as well as its other substrates. This effect of heparin is the basis for its clinical use as an anticoagulant. The naturally occurring heparin activator of antithrombin III is present as heparin and heparin sulfate on the surface of vessel endothelial cells. It is this feature that controls the activation of the intrinsic coagulation cascade.

However, thrombin activity is also inhibited by α2-macroglobulin, heparin cofactor II and α1-antitrypsin. Although a minor player in thrombin regulation α1-antitrypsin is the primary serine protease inhibitor of human plasma. Its physiological significance is demonstrated by the fact that lack of this protein plays a causative role in the development of emphysema.

Activation of Fibrinogen to Fibrin

Fibrinogen (factor I) consists of 3 pairs of polypeptides ([A-α][B-β][γ])$_2$. The 6 chains are covalently linked near their N-terminals through disulfide bonds. The A and B portions of the A-α and B-β chains comprise the fibrinopeptides, A and B, respectively. The fibrinopeptide regions of fibrinogen contain several glutamate and aspatate residues imparting a high negative charge to this region and aid in the solubility of fibrinogen in plasma. Active thrombin is a serine protease that hydrolyses fibrinogen at four arg-gly bonds between the fibrinopeptide and the a and b portions of the protein.

Thrombin-mediated release of the fibrinopeptides generates fibrin monomers with a subunit structure $(\alpha-\beta-\gamma)_2$. These monomers spontaneously aggregate in a regular array, forming a somewhat weak fibrin clot. In addition to fibrin activation, thrombin converts factor XIII to factor XIIIa, a highly specific transglutaminase that introduces cross-links composed of covalent bonds between the amide nitrogen of glutamines and e-amino group of lysines in the fibrin monomers.

Dissolution of Fibrin Clots

Degradation of fibrin clots is the function of plasmin, a serine protease that circulates as the inactive proenzyme, plasminogen. Any free circulating plasmin is rapidly inhibited by α2-antiplasmin. Plasminogen binds to both fibrinogen and fibrin, thereby being incorporated into a clot as it is formed. Tissue plasminogen activator (tPA) and, to a lesser degree, urokinase are serine proteases which convert plasminogen to plasmin. Inactive tPA is released from vascular endothelial cells following injury; it binds to fibrin and is consequently activated. Urokinase is produced as the precursor, prourokinase by epithelial cells lining excretory ducts. The role of urokinase is to activate the dissolution of fibrin clots that may be deposited in these ducts.

Active tPA cleaves plasminogen to plasmin which then digests the fibrin; the result is soluble degradation product to which neither plasmin nor plasminogen can bind. Following the release of plasminogen and plasmin they are rapidly inactivated by their respective inhibitors. The inhibition of tPA activity results from binding to specific inhibitory proteins. At least four distinct inhibitors have been identified, of which 2-plasminogen activator-inhibitors type 1 (PAI-1) and type 2 (PAI-2) are of greatest physiological significance.

Thus, from the above it can be seen that the physiological mechanisms involved in coagulation are exceedingly complex, and it will be appreciated that great difficulty exists in designing or identifying agents that are capable of safely modulating the many inter-related pathways in coagulation. The multilevel cascade of blood clotting system permits enormous amplification of its triggering signals. Moving down the extrinsic pathway, for example, proconvertin (VII), Stuart factor (X), prothrombin, and fibrinogen are present in plasma in concentrations of <1, 8, 150, and ~4000 mg·mL$^{-1}$, respectively. Thus a small signal is very quickly amplified to bring about effective hemostatic control.

Clotting must be very strictly regulated because even one inappropriate clot can have fatal consequences. Indeed, blood clots are the leading cause of strokes and heart attack, the two major causes of human death. Thus, the control of clotting is a major medical concern. Several inhibitors have been developed with different mechanisms of anticoagulant action. These include the heparins, the coumarins, and the 1,3-indanediones.

Heparin is a mucopolysaccharide with a molecular weight ranging from 6,000 to 40,000 Da. The average molecular of most commercial heparin preparations is in the range of 12,000-15,000. The polymeric chain is composed of repeating disaccharide unit of D-glucosamine and uronic acid linked by interglycosidic bonds. The uronic acid residue could be either D-glucuronic acid or L-iduronic acid. Few hydroxyl groups on each of these monosaccharide residues may be sulfated giving rise to a polymer with that is highly negatively charged. The average negative charge of individual saccharide residues is about 2.3.

The key structural unit of heparin is a unique pentasaccharide sequence. This sequence consists of three D-glucosamine and two uronic acid residues. The central D-glucosamine residue contains a unique 3-O-sulfate moiety that is rare outside of this sequence.

Heparin forms a high-affinity complex with antithrombin. The formation of antithrombin—heparin complex greatly increases the rate of inhibition of two principle procoagulant proteases, factor Xa and thrombin. The normally slow rate of inhibition of both these enzymes ($\sim 10^3$-$10^4$ M-1 s-1) by antithrombin alone is increased about a 1.000-fold by heparin. Accelerated inactivation of both the active forms of proteases prevents the subsequent conversion of fibrinogen to fibrin that is crucial for clot formation.

Heparin is relatively non-toxic, however heparin overdose or hypersensitivity may result in excessive bleeding. Protamines, are used as anti-dote for excessive bleeding complications.

Coumarin and its derivatives are principal oral anticoagulants. Warfarin is a coumarin derivative marketed as a racemic mixture of R and S isomers.

Coumarins are slow to act, exerting their effect in vivo only after a latent period of 12 to 4 hours and their effect lasts for 1.5 to 5 days. The observed slow onset may be due to the time required to decrease predrug prothrombin blood levels, whereas the long duration of action observed with warfarin may be due to the lag time required for the liver to resynthesize prothrombin to predrug blood levels.

Coumarins and 1,3-indandiones (see infra) have a further disadvantage in that they interact with certain drugs. For example, the action of oral anticoagulants can be enhanced by drugs such as phyenylbutazone and salicylates while antagonized by barbiturates and vitamin K. Coumarins are competitive inhibitors of vitamin K in the biosynthesis of prothrombin.

The coagulation cascade relies on the conversion of prothrombin to thrombin in a very important step. However, this conversion depends on the presence of 10 g-carboxyglutamic acid (GLA) residues in the N-terminus of prothrombin. The multiple Gla residues form a binding site for $Ca^{2+}$. Under normal circumstances 10 glutamic acid (Glu) residues of prothrombin are converted to Gla residues in a post-translational modification.

This post-translation modification is catalyzed by an enzymes vitamin K reductase and vitamin K epoxide reductase. Vitamin K is a co-factor in this conversion reaction. Thus it cycles between a reduced form and an epoxide form. Because of their structural similarity with vitamin K coumarins are thought to bind the enzymes, vitamin K reductase and vitamin K epoxide reductase, without facilitating the conversion of Glu residues of prothrombin to Gla. Thus prothrombin cannot be acted upon by factor Xa.

The 1,3-indanediones have been known in the art to be anticoagulant since the 1940s. The onset and duration of action of anisindione are similar to those for coumarins. The chief disadvantage of indandiones is their side effects. Some patients are hypersensitive to it and develop a rash, pyrexia, and leukopenia.

Despite the overall benefits achieved, the currently used therapeutic anticoagulants are also a major source of mortality and morbidity, caused by limitations in efficacy and even more so by bleeding complications. In an effort to overcome these problems, a number of new agents have been developed. However, it appears that therapeutic anticoagulation inevitably comes with the inherent problem that increased efficiency is only achieved by an increase in bleeding complications. Targeting of anticoagulants to the clot may represent a means to break this fatal linkage. The fusion of anticoagulants to antibodies that are directed against clot-specific epitopes allows enrichment of the anticoagulants at the clot whereas the concentration of the anticoagulants in the circulating blood can be kept at a low level.

The success of clot targeting is dependent on the abundance and specificity of the epitope chosen as target. It has been previously demonstrated that fibrin, may be used for clot targeting. However fibrin or fibrin degradation products may circulate in the blood leading to mis-targeting of anticoagulants in the circulation.

A further problem in the art relates to the diagnosis of clotting disorders. It is accepted that many clotting disorders may be prevented or at least prevented from advancing to a more serious problem. It is therefore desirable for the clinician to have an indicator of early clotting disorders.

It is an aspect of the present invention to overcome or alleviate a problem of the prior art by providing an anticoagulant agent that is efficacious, yet does not result in extended clotting time. The present invention further provides methods and reagents for diagnosing a clotting-related disorder.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In one aspect, the present invention provides an anticoagulant agent including a first element capable of inhibiting coagulation and a second element capable of targeting an activated platelet wherein upon administration of the agent to a subject the second element directs the first element to the activated platelet. Applicants have demonstrated that targeting of anticoagulants to activated platelets provides a means to inhibit coagulation without the danger of excessive bleeding. In one form of the invention the second element is targeted against ligand-induced binding sites (LIBS) on the activated, fibrinogen/fibrin-binding GP IIb/IIIa represent a clot-specific target, which is abundantly and specifically expressed on clots. For clot-targeting, an anti-LIBS single-chain antibody (scFv$_{anti-LIBS}$) was produced. As the first element, a highly potent, direct factor Xa (fXa) inhibitor, the tick anticoagulant peptide (TAP) was used. Specific antibody binding of the fusion molecule scFv$_{anti-LIBS}$-TAP was proven in flow cytometry, and anti-fXa activity was demonstrated in chromogenic assays. In vivo anticoagulative efficiency was determined as occlusion time (OT) by doppler flow measurements in a ferric-chloride induced thrombosis model of the carotid artery in mice. scFv$_{anti-LIBS}$-TAP prolonged OT comparable to enoxaparin, and equimolar doses of recombinant TAP, and a non-targeted mutant-scFv-TAP, even at low doses where the latter control did not reveal antithrombotic effects. In contrast to the other anticoagulants tested, bleeding time as measured by tail transection was not prolonged by scFv$_{anti-LIBS}$-TAP.

The present invention also provides pharmaceutical compositions, and methods for treating or preventing a coagulation disorder, said method including the steps of administering to a mammal in need thereof an effective amount of a composition as described herein. Also included are diagnostic methods for screening compounds useful as anticoagulants, and methods for identifying the presence of thrombosis, thrombotic emboli, unstable plaques, and the like using probes directed to activated platelets.

BRIEF DESCRIPTION OF THE FIGURES

FIG. 1 shows the ScFv-anti-LiBS-TAP (SEQ ID NO: 1; SEQ ID NO: 2): The Signal Peptide Sequence of Bacterial Pectate Lyase (pelB) includes the nucleotides from position 40 to position 105, the variable region of the heavy chain includes nucleotides from position 106 to position 483, the Linker (YOL epitope) includes nucleotides from position 484 to position 510; the variable region of the light chain includes nucleotides from position 511 to position 861; the TAP region includes nucleotides from position 862 to position 1041, and the His6-tag commences at position 1069 and terminates at position 1086.

FIG. 10 Left panel: Confocal microscopy of the adhesion assay. P-Selectin and fluorescein avidin-stained platelets appear as green conglomerates, surrounded by the red fluorescent beads of the anti-LIBS bead contrast agent. Right panel: 3D-reconstruction of a Z-stack from 60 images of confocal microscopy.

FIG. 15A to FIG. 15D show histology of representative injured femoral artery segments. (A) shows multiple bead-binding to the injured wall after perfusion with LIBS-MPIO (arrows), whereas no binding can be observed after Control-MPIO perfusion (B). Tissue of (A) and (B) was iron-stained, although polystyrene-coating of the beads allow typical blue staining of the iron core. However, blue intrinsic signal of the iron core could be observed depending upon the focus of the microscope. (C) Binding of the LIBS-MPIO contrast agent to platelets was confirmed using immunohistochemistry for CD61 and NovaRed stain. (a) represents a wall-adherent platelet and (b) a MPIO bound directly to the platelet. (D) Quantification of MPIOs bound per representative histology-section in LIBS-MPIO and Control-MPIO perfused mice, showing highly specific binding of the LIBS-targeted contrast agent ($p<0.01$).

DETAILED DESCRIPTION OF THE INVENTION

Figure 2:
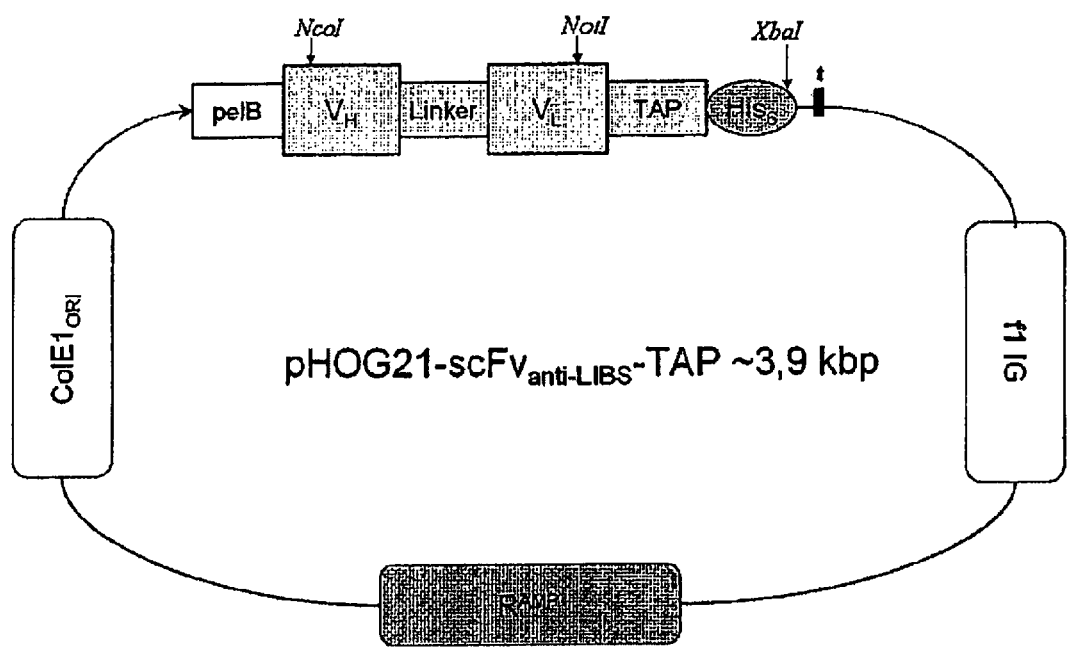
FIG. 2 shows a map of pHOG21-scFvanti-LIBS-TAP. RAMP: ampicillin resistance gene; ColE1OR1: origin of replication of E. coli; f1 IG, filamentous intergenic region; pelB: leader peptide sequence of pectate lyases pelB; VH/VL: heavy/light chain; TAP: tick anticoagulant peptide; His6: repeat of 6 histidines.

In a first aspect, the present invention provides an anticoagulant agent including a first element capable of inhibiting coagulation and a second element capable of targeting an activated platelet wherein upon administration of the agent to a subject the second element directs the first element to the activated platelet. Applicants have found that by targeting anticoagulants to activated platelets the nexus between increased anticoagulant efficacy and bleeding complications is broken, thereby overcoming a significant problem in the art. Applicants have found that activated platelets can be used as an effective target for efficient clot-targeting. Platelets are highly abundant in particular in thrombi within the arterial system, as with atherosclerosis-induced thrombi e.g. in myocardial infarction. Activated platelets are highly specific for clots and are typically not found in the circulation. Thus, both requirements for efficient clot-targeting, abundance and specificity, are satisfied. Besides these favorable properties, the use of activated platelets as epitopes for clot-targeting may be further advantageous compared to fibrin, since platelet activation may precede fibrin formation.

The anticoagulant agent may take any form, so long as the two elements are capable of performing their required functions as described supra.

The anticoagulant element may be any size so long as the agent is able to effectively localize at the site of a clot. However, the anticoagulant element is preferably small, since this may improve thrombus accessibility and penetration. In a preferred form the invention the first element has a molecular weight of about 7,000 Da or less. While the prior art discloses a number of small anticoagulants, It is preferred that it potently inhibit a central and important coagulation factor. In one form of the invention the first element is a peptide anticoagulant derived from the soft tick Orinthodoros moubata that uses an anti-factor Xa inhibitor to facilitate extraction of blood from its host. This anticoagulant was initially described in 1990 (Waxman et al. Science 1990; 248: 2473) and named TAP (tick anticoagulant peptide). Recombinant TAP has been described as a selective factor Xa inhibitor allowing effective anticoagulation because of the central, up-stream, and rate-determining position of factor Xa in the coagulation cascade (Neeper et al. J Biol Chem 1990; 265: 17746). TAP is one of the most potent anticoagulants found in nature and it is a small molecule with only 60 amino acids. The sequence of a suitable TAP is available from the Genbank database under accession number M60480.

The first element may act upon any component of either the extrinsic or intrinsic coagulation pathways. In a preferred form of the invention the first element acts on the enzyme factor Xa. Direct inhibition of fXa has been proposed to be advantageous compared to the indirect, antithrombin-III-mediated inhibition, e.g. as mediated by heparins, since clot-bound fXa and prothrombinase-associated fXa seem to be significantly better inhibited by direct fXa inhibitors. In comparative studies investigating anti-thrombotic potency and the prevention of re-occlusion, TAP has been shown to be advantageous to indirect fXa inhibitors as well as to thrombin inhibitors. Despite these advantages, high bleeding rates were expected for a therapeutic use in humans, similar to hirudin, and the development for a human drug has not been preceded. Without wishing to be limited by theory targeting of TAP to developing clots could decrease systemic anticoagulation and thus bleeding complications and a long lasting local anticoagulative effect may be achievable due to a stable fixation of anti-fXa activity at the clot. Thus, TAP being a small molecule, demonstrating a direct inhibition with no need for a cofactor, and targeting the early centre of the coagulation pathway is a preferred candidate for targeting.

While TAP is used in one embodiment of the invention, many other anticoagulants will be suitable, including other inhibitors of coagulation factors such as hirudin. Also the targeting of fibrinolytics promises highly efficient thrombolysis with less bleeding complications.

As used herein, the term "inhibiting coagulation" is intended to mean not only a complete inhibition, but also a partial inhibition of clot formation. Without wishing to be limited by theory, it is contemplated that a partial inhibition is preferable since complete inhibition may lead to uncontrolled bleeding.

The function of the second element is to bring the first element into physiological proximity to the activated platelet. This may be accomplished by the second element having the ability to bind to the activated platelet, or to bind to a molecule associated with the activated platelet. Typically, this will be achieved by the second element being capable of binding to a marker on the surface of an activated platelet. To afford the agent the highest possible specificity, the marker should be one that is expressed only on the surface of activated platelets. However it will be understood that such an absolute requirement is not strictly necessary, and so long as the second element is capable of targeting predominantly activated platelets, then the invention will provide the advantages disclosed herein.

There are a number of markers that are predominant on activated platelets including activated GPIIb/IIIa. The marker may be one that takes an inactive and an active form such that one form is found to predominate over the other in activated platelets, as compared with other components of the coagulation system. One of the most abundantly expressed molecules on the platelet surface is the glycoprotein receptor (GP) IIb/IIIa (CD41/CD61). This receptor belongs to the adhesion molecule family of integrins and is also termed $\alpha_{IIb}\beta_3$. Integrins consist of two non-covalently linked subunits that undergo a conformational change from a low affinity to a high affinity receptor in respect to the binding of the GPIIb/IIIa ligand fibrinogen. Besides the exposure of the ligand binding pocket, this conformational change also induces the exposure of so-called ligand-induced binding sites (LIBS) on GPIIb/IIIa. These binding sites are specific for the activated and/or ligand bound GP IIb/IIIa receptor. GPIIb/IIIa is highly abundant with around 60 000 to 80 000 molecules on the surface of each platelet.

This receptor is transformed from an inactive state to an active state upon platelet activation, the mechanism of which is a conformational change of the receptor such that new epitopes are exposed. Thus, in one form of the invention the second element is capable of binding to a new epitope formed upon activation of the GP IIb/IIIa receptor.

The skilled person will appreciate that it is not strictly necessary for the first and second elements to be physically linked. For example the first and second elements may be physically separate, with the first element including means for binding to the second element. Under this proposal, the first element may be administered first to the subject, and travel to a new clot to bind to the activated platelet. The second element may then be administered, and bind to the first element. Thus, the two elements are physically separate until a functional anticoagulation agent is achieved at the site of the activated platelet.

In a preferred form of the invention the anticoagulation agent is in the form of a single molecule, and typically a single protein molecule. A convenient means for achieving the two elements in a single molecule is by including both elements in the framework of a single-chain antibody molecule. These molecules are particularly suitable for specifically targeting epitopes given their inclusion of a variable region. The variable region is designed such that it has an affinity for the targeted epitope. Single-chain antibodies are a promising format for the design of recombinant therapeutic agents. They consist of only the variable regions of the antibodies' heavy and light chains fused together via a short linker molecule on a single peptide chain. Thus, single-chain antibodies (scFvs) comprise the smallest fragments containing a complete antibody binding site. Since size is a determinant of immunogenicity, it is expected that scFvs are only minimal, if at all, immunogenic.

Another advantage of single chained antibodies is that coupling of the first and second elements leads to little loss of biological function of the elements. It will be appreciated however that chemical coupling typically results in a significant loss of both the antibody binding function as well as of the activity of the coupled effector molecules, scFv can be coupled without functional loss using molecular biology techniques. Finally, scFvs can be produced in bacteria in large quantities, in a short period of time, at low cost, and they can be highly purified by affinity chromatography. Means for producing single chained antibodies are well known to the skilled person with a review on the topic being found in Recombinant Antibodies (Breitling & Duebel, 1999, Publisher: Wiley & sons, ISBN 0471178470), the contents of which is herein incorporated by reference.

Preferably, the cloning of an anti-LIBS single-chain antibody (scFv) based on a hybridoma cell line expressing IgG anti-LIBS 145. An antibody against a LIBS (ligand-induced binding sites) epitope was chosen for the targeting of anticoagulants to clots. As previously demonstrated, the mAb anti-LIBS 145 ($IgG_{anti-LIBS}$) demonstrates ligand-induced binding to GPIIb/IIIa after incubation of platelets with RGD-peptides, abciximab, tirofiban and eptifibatide (Schwarz et al. JPET 2004, 308: 1002). Furthermore, $IgG_{anti-LIBS}$ demonstrate a strong binding to ADP-activated platelets in the presence of fibrinogen (FIG. 2). Thus, this antibody provides a targeting propensity that is highly abundant and specific.

Figure 3:
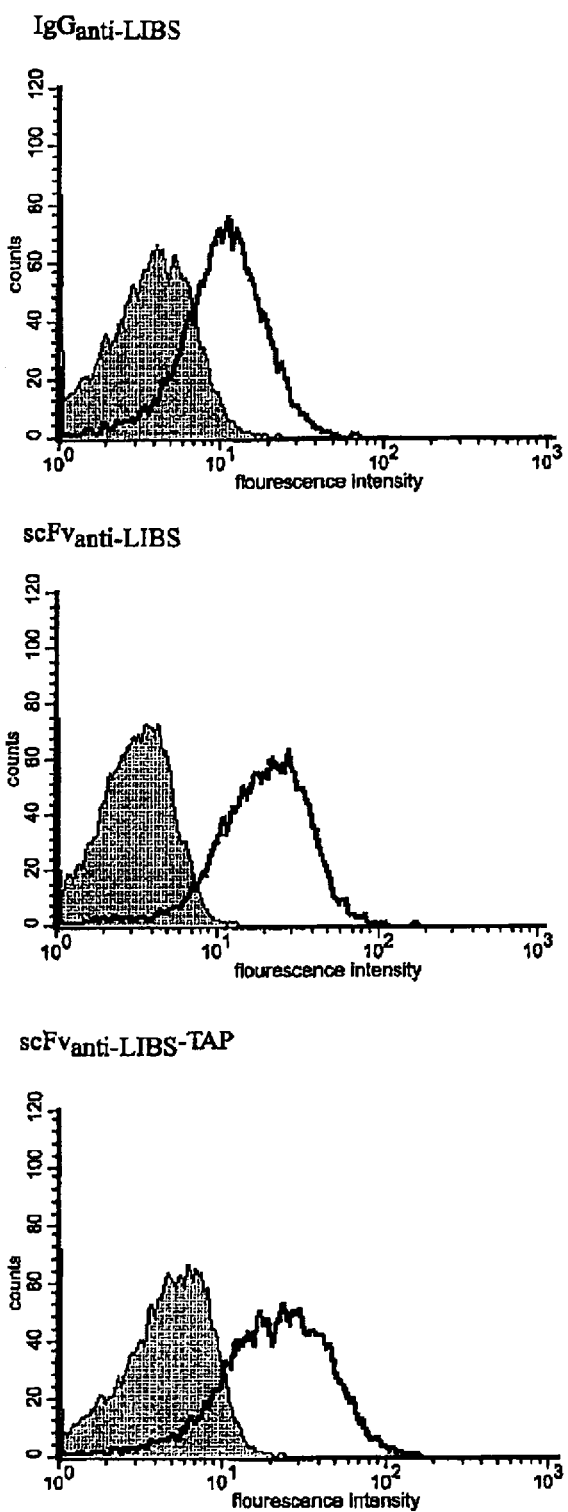
FIG. 3 shows flow cytometry histograms of specific binding of IgG anti-LIBS, scFv anti-LIBS, and scFv anti-LIBS-TAP to activated but not to non-activated human platelets. Binding of ADP-activated platelets is given by open histograms; binding to non-activated platelets is given by shaded histograms. Binding of the IgG antibody is detected by a DTAF-conjugated goat anti mouse antibody, binding of the scFvs is detected by an Alexa Fluor 488 conjugated anti-His tag antibody.

The mAb anti-LIBS 145 expressing hybridoma cell line was used as the basis for the cloning of an anti-LIBS single-chain antibody (scFv). mRNA of this hybridoma cell line was prepared and reverse transcribed using an oligo-dT primer. The variable regions of the antibody's heavy and light chain were amplified by PCR using primers that anneal to conserved regions (see methods described elsewhere herein for detail) at the 5' and 3' ends of the variable regions. The PCR products were cloned into the pHOG21 expression vector that allows high-level expression in bacteria. After transformation of TG1 E. coli individual clones were assessed for LIBS-typical binding to GP IIb/IIIa. One clone that revealed a stronger binding compared to the original IgG anti-LIBS 145 mAb in flow cytometry (FIG. 2) was chosen for further use. This clone was sequenced and it revealed all the typical features of a single-chain antibody (FIG. 1). Furthermore, Western blot analysis revealed the correct size with around 32 kDa (FIG. 3).

Preferably, the single chain antibody is expressed as a scFv fusion protein. Based on previous results showing that TAP can be fused without functional loss (TH), this highly potent direct factor Xa inhibitor was chosen to couple with the cloned single-chain antibody. TAP was originally synthesized according to published sequence information (Genbank database under accession number M60480) and was cloned into the pHOG21 expression vector directly at the C-terminus of the variable region of the light chain (see FIG. 1). pHOG21 contains a pelB-leader-sequence facilitating purification via inclusion bodies and a His(6)-tag for $Ni^{2+}$-purification as well as detection (FIG. 1). The yield of purified $svFv_{anit-LIBS}$-TAP was around 0.4 to 0.8 mg from 1 L bacterial culture. After expression and purification, the size of the single-chain antibody constructs was assessed by Western blot analysis (FIG. 3). The molecular weight of the alone was ~32 kDa, of the intact fusion protein $svFv_{anti-LIBS}$-TAP was ~39 kDa, and of the non-targeted mut-scFv-TAP was ~42 kDa (FIG. 3).

In a highly preferred form of the invention, the single-chain antibody is essentially as shown in FIG. 1. The skilled person will understand that the degeneracy of the genetic code and the ability to substitute amino acids for other similar amino acids means that derivatives and equivalents of the molecule specified by FIG. 1 can be easily generated. These derivatives and equivalents are included in the scope of the present application.

In another aspect, the present invention provides a pharmaceutical composition including an anticoagulant agent as described herein. The skilled person will be enabled to devise compositions suitable for delivering the anticoagulant agents described herein by routine methods. Where the anticoagulation agent is a protein the composition may simply contain NaCl at an isotonic concentration. It may be necessary to add carrier proteins, stabilizers, buffers, non-aqueous solvents, salts, preservatives and the like.

In another aspect the present invention provides a method for treating or preventing a coagulation disorder, said method including the steps of administering to a mammal in need thereof an effective amount of a composition as described herein. Typically, the composition will be administered systemically by intravenous or intra-arterial boli or infusion. In terms of dosage, where the anticoagulant agent is a protein the dosage is between about 30 mg/kg to about 300 mg/kg. It is well within the ability of a clinician to titrate the dosage upwards or downwards to achieve the desired clinical effect for any given subject, or for any given disorder of coagulation.

The coagulation disorder may be any disorder that requires an inhibition of coagulation. Such disorders include all clinical settings that are associated with thrombosis such as coronary artery disease, acute coronary syndrome including myocardial infarction, stroke, atherosclerosis of the carotid artery or aorta, deep vein thrombosis, pulmonary embolism, and atherosclerosis or thrombosis of an organ.

Figure 4:
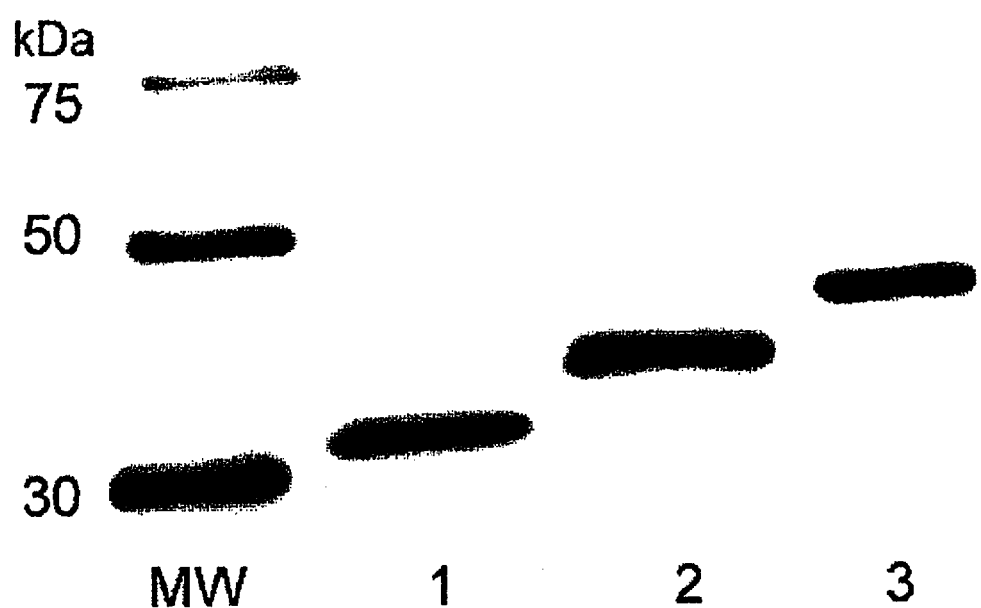
FIG. 4 shows Western blot analysis of Ni 2+-purified scFv anti-LIBS, scFv anti-LIBS-TAP, and non-targeted mut-scFv-TAP. MW: molecular weight marker (6×His protein ladder), 1: scFv anti-LIBS, 2: scFv anti-LIBS-TAP, 3: non-targeted scFv-TAP.

The preferred bi-functional fusion molecule $scFv_{anti-LIBS}$-TAP has been evaluated by the Applicant. The function of the single-chain antibody part of the fusion molecule $scFv_{anti-LIBS}$-TAP was evaluated by flow cytometry. $ScFv_{anti-LIBS}$-TAP and $scFv_{anti-LIBS}$ demonstrated similar binding properties to fibrinogen-bound, activated platelets (FIG. 2). Thus, the genetic fusion did not significantly alter the single-chain antibody's binding property. The factor Xa inhibitory activity of the fusion constructs was evaluated by a chromogenic assay. Factor Xa was incubated with a specific chromogenic substrate in the presence of $scFv_{anti-LIBS}$-TAP, non-targeted mut-scFv-TAP, $scFv_{anti-LIBS}$ and recombinant TAP (FIG. 4). Compared to rTAP, TAP activity was slightly reduced in the fusion constructs, but was clearly present (FIG. 4). Thus, both functions, antibody binding and factor Xa inhibition were retained.

Figure 5:
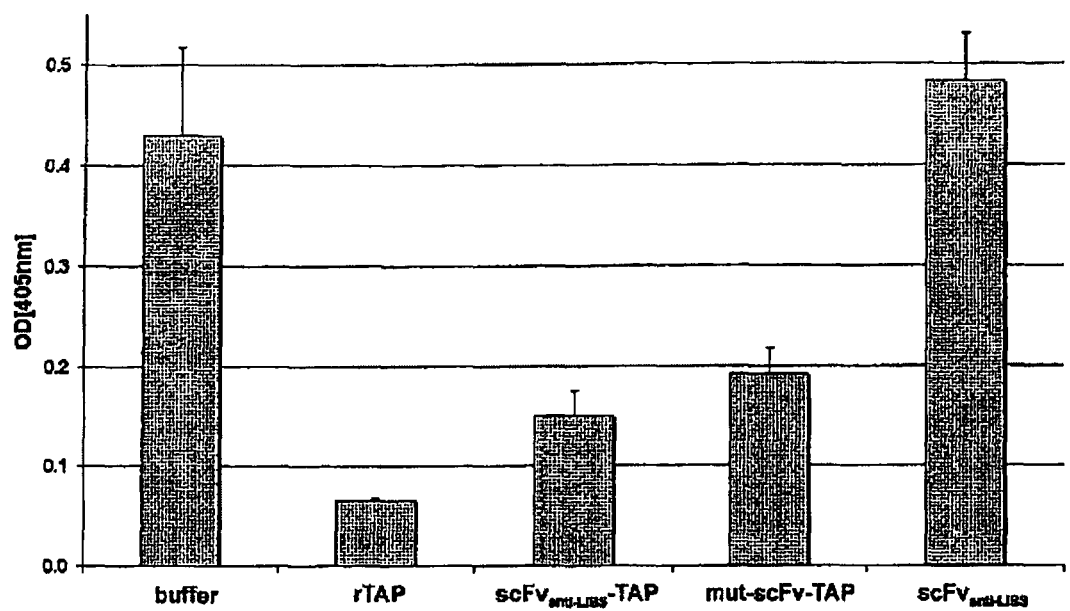
FIG. 5 shows inhibition of factor Xa activity by rTAP, scFv anti-LIBS-TAP, and non-targeted mut-scFv-TAP, but not by scFv anti-LIBS. The cleavage of chromogenic substrate (spectrozyme FXa #222) by factor Xa (500 pM) was determined at 405 nm. Bars show optical density (OD) as mean and standard deviation of triplicate measurements of a representative experiment.

To show superiority of the targeting of anticoagulants to the LIBS epitopes of GP IIb/IIIs on activated platelets compared to the conventional, non-targeted use of anticoagulant a well-established mouse thrombosis model was chosen (Farrehi et al. 1998; 97:1002). However, it was first demonstrated that the anti-LIBS antibodies could be used for targeting to fibrinogen-bound, activated platelets of mice. Applicants obtained mouse blood and evaluated the binding of the original $IgG_{anti-LIBS}$, of the $scFv_{anti-LIBS}$, and of the fusion construct $scFv_{anti-LIBs}$-TAP to mouse platelets by flow cytometry. Similar to the results in human platelets, a specific binding of the $IgG_{anti-LIBS}$ was seen, but an even stronger specific binding was noted with the $scFv_{anti-LiBs}$ antibody alone as well as binding of its fusion protein $scFv_{anti-LBS}$-TAP to fibrinogen-bound, activated mouse platelets (FIG. 5). Thus, it is proposed that targeting of mouse platelets will work with the generated anti-LIBS fusion constructs.

Figure 8:
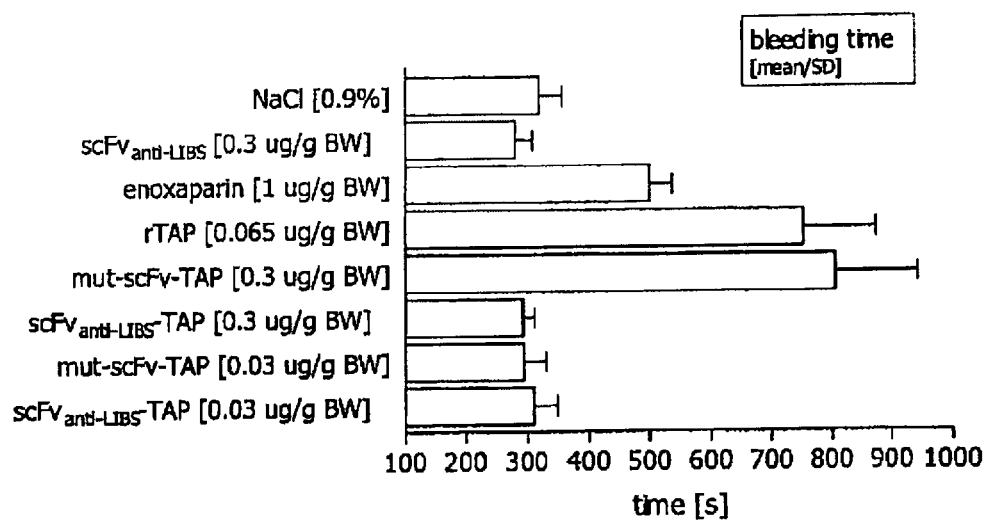
FIG. 8 shows the clot-targeted anticoagulant scFv anti-LIBS-TAP does not cause bleeding time prolongation in contrast to enoxaparin, rTAP, and non-targeted mut-scFv-TAP. Bleeding time in mice was determined by tail transection. Saline (0.9% NaCl) and the single-chain antibody scFv anti-LIBS are used as negative control. rTAP and non-targeted mut-scFv-TAP demonstrated considerable prolongation of bleeding time in contrast to scFv anti-LIBS-TAP. Mean and standard deviation (SD) of 4 mice per group are given.

Thrombi were induced in the carotid artery of mice using ferric chloride. The termination of blood flow measured by a nano flow probe was used as an indicator of an occlusive thrombus in the vessel. Sodium chloride solution and the single-chain antibody anti-LIBS were used as a negative controls and enoxaparin was used as a positive control representing the current clinical standard. Enoxaparin nearly doubled the occlusion time (FIG. 8). Equimolar amounts of recombinant TAP, non-targeted mut-scFv-TAP and $scFv_{anti-LIBS}$-TAP caused significant prolongation of the occlusion time close to the effects of enoxaparin. A reduction to 1/10 (0.03 μg/g body weight) of the original dose delivered still caused a significant prolongation of the occlusion time (p=0.002) with the $scFv_{anti-LIBS}$-TAP, whereas the non-targeted mut-scFv-TAP at the same dose did not cause a significant prolongation of the occlusion time. Thus, the $scFv_{anti-LIBS}$-TAP delivers a strong anticoagulant effect, even at a dose at which the direct control, the non-targeted mut-scFv-TAP does not cause significant anticoagulation.

Figure 6:
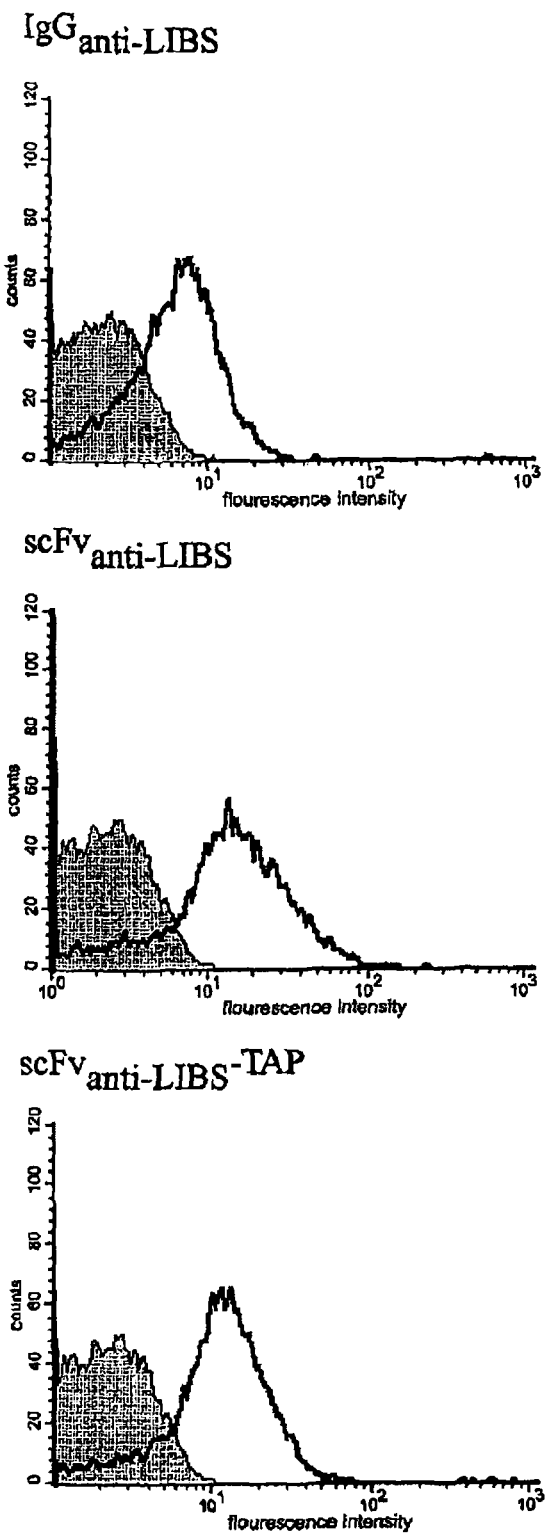
FIG. 6 shows flow cytometry histograms of specific binding of IgG anti-LIBS, scFv anti-LIBS, and scFv anti-LIBS-TAP to activated but not to non-activated mouse platelets. Binding of thrombin-activated platelets is given by open histograms; binding to non-activated platelets is given by shaded histograms. Binding of the IgG antibody is detected by a DTAF-conjugated goat anti-mouse antibody, binding of the scFvs is detected by an Alexa Fluor 488 conjugated anti-His tag antibody.
Figure 7:
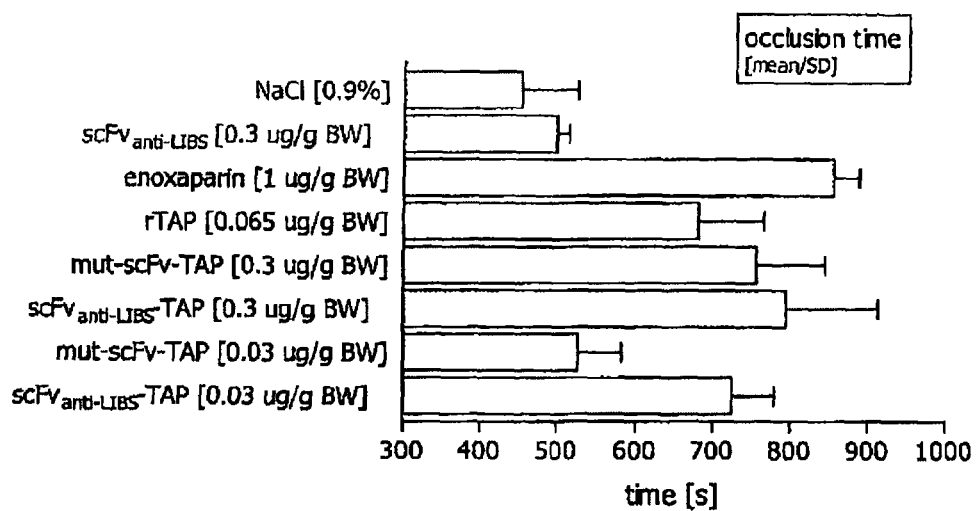
FIG. 7 shows antithrombotic effects of scFv anti-LIBS-TAP at high and low doses in a mouse model with ferric chlorid-induced thrombosis in the carotid artery. Thrombus development was evaluated by occlusion time measurements as determined by flow measurement with a nano doppler flow probe at the carotid artery. Saline (0.9% NaCl) and the single-chain antibody scFv anti-LIBS are used as negative control. Enoxaparin as a clinically used agent is used as a positive control. rTAP, scFv anti-LIBS-TAP, and non-targeted mut-scFv-TAP were used at a high equimolar dose and scFv anti-LIBS-TAP and non-targeted scFv-TAP were used at a low equimolar dose. Mean and standard deviation (SD) of 4 mice per group are given.

A major advantage of activated platelet-targeted anticoagulation is a reduction of bleeding complications. Bleeding time was determined by a standardized surgical tail transection in mice. As expected, saline and $scFv_{anti-LIBS}$ did not cause bleeding time prolongations, whereas enoxaparin, and in particular recombinant TAP caused a considerable prolongation. At the dose of 0.3 μg/g BW at which both, non-targeted mut-scFv-TAP and $scFv_{anti-LIBS}$-TAP demonstrated a strong anticoagulant effect (FIG. 6), only the non-targeted mut scFv-TAP caused a highly significant prolongation in bleeding time (p<0.001, FIG. 7). The clot-targeted $scFv_{anti-LIBS}$-TAP did not cause a prolongation in the bleeding time at all. Also the lower dose of $scFv_{anti-LIBS}$-TAP, which still demonstrated a clear anticoagulant effect at the carotid artery of the mouse, did not cause bleeding time prolongation. Thus, highly effective anticoagulative effects could be achieved by the newly generated fusion of TAP to the anti-LIBS single-chain antibody without prolongation of bleeding time.

It will be appreciated that while avoidance of prolongation of bleeding time is an advantage of the present invention, the anticoagulant agents described herein may increase bleeding time in some embodiments.

In another aspect the present invention provides the use of an anticoagulant agent as described herein in the preparation of a medicament for the prevention or treatment of a coagulation disorder.

In a further aspect the present invention provides a method of screening for a compound useful for targeting an anticoagulant to a clot, said method including the steps of providing a candidate compound, exposing the compound to an activated platelet and at least one other component of a clot, assessing whether the compound binds to the activated platelet, and assessing whether the compound binds to the at least one other component of a clot wherein the compound is useful if it is capable of higher affinity binding to the activated platelet as compared the at least on other component of a clot.

Thus, it will be possible to identify compounds useful as a second element in the context of the present invention based on the Applicant's finding that activated platelets are an advantageous target for anticoagulation therapy. The skilled artisan will be familiar with a number of methods useful in determining the binding of one molecule to another, including immunoadsorbent methods, chromatographic methods, surface plasmon resonance methods and the like.

In a further aspect the present invention provides a compound identified by a screening method described herein.

Another aspect of the present invention provides a method of diagnosis or prognosis of a coagulation disorder in a subject, the method including the detection of an activated platelet in a blood vessel of the subject.

To the best of the Applicant's knowledge, the prior art fails to disclose the use of activated platelets for diagnosis or prognosis. The detection of activated platelets will provide the clinician with a relevant marker useful in a number of medical applications. One application is to image activated platelets found on ruptured coronary plaques or those plaques that are prone to rupture. This will allow for an early non-invasive diagnosis of such as myocardial infarction syndromes with following prophylactic implantation of stents into relevant lesions possible. This is of special clinical interest as coronary angiography (as described in the prior art) only provides information about the vessel lumen, but not about the morphology of the vessel wall itself. Thus, possibly ruptured or rupture-prone plaques are not detected with coronary angiography.

In consideration of the usefulness of activated platelets as a diagnostic marker, the present invention also provides a probe for detecting a blood vessel abnormality including (a) a binding element capable of targeting an activated platelet and (b) a label. The skilled person will understand that probes useful in the context of the present invention are typically provided as an aqueous composition and injected into an artery or a vein of the subject prior to or during the diagnostic method. The probe is then transported to the site of interest in the body by the blood and binds to an activated platelet if present. The bound probe is then detected by an appropriate means such as MRI.

The binding element may be capable of binding to a marker on the surface of an activated platelet. A non-limiting example of a suitable marker is the activated GPIIb/IIIa receptor molecule. Other markers such as PAC-1 and CD62-P are also contemplated. In one form of the invention the binding element and label are in the framework of a single-chain antibody molecule.

The probes and methods using the probes described herein may be used to detect any accumulation of activated platelets, for example in pulmonary or peripheral embolism, or on ruptured atherosclerotic plaques in peripheral or cerebral arteries. These lesions could be detected early in the disease process and selectively treated.

The skilled person will understand that the probes and methods described herein may be useful in identifying individuals having a predisposition to a coagulation disorder, without necessarily demonstrating as a clinically recognizable sign or symptom of a coagulation disorder.

In a preferred form of the method, the probe used for the step of detecting an activated platelet is a single-chained antibody as described herein. Preferably the single-chained antibody is the same or similar to the anti-LIBS antibody as described herein. It will be appreciated that for diagnostic purposes, the single-chained antibody does not need to include the anticoagulant component. Indeed, the skilled person will understand that it may be possible to use a fragment of the single-chained antibody, so long as that fragment includes the site responsible for binding to activated platelets. Without wishing to be limited by theory it is thought that the compact dimensions of a single-chain antibody is of particular advantage in this application. It is proposed that the antibody is capable of penetrating beyond the surface of a thrombus into areas where a greater number of activated platelets are present. This allows for more effective detection of the bound antibody, and therefore higher sensitivity imaging. The antibody probe may also adhere to the surface of a blood vessel where an activated platelet has deposited.

The method may be used to diagnose and identify thrombi (e.g. deep vein thrombosis), thrombotic emboli (e.g. pulmonary embolism) and deposition of activated platelets (e.g. at the site of unstable atherosclerotic plaques). Early detection will be highly advantageous allowing the administration of clot dissolving agents and/or anticoagulant therapy and/or interventional procedures.

The skilled artisan will understand that the probe used for diagnostic and prognostic methods may be labelled by any method known in the art. Depending on the functionalization of the particles, different strategies can be used for this purpose. One way is to build peptide bonds between carboxy-functionalized SPIOs and free amino groups of the single-chain antibody. The skilled person is familiar with a range of commercially available coupling agents and kits that may be used for this chemical crosslinking approach. Another way would be to use the histidine-tag of the antibody for conjugation with commercially available cobalt-functionalized 1 μm SPIO-beads, whereby the single-chain antibody/bead complex is maintained by the binding of histidine to cobalt. Briefly, with this approach single-chain antibodies and SPIO-beads are incubated at room temperature for 10 minutes, thereafter the suspension is separated by a magnet and washed several times. Appropriate controls are generated by conjugating an irrelevant single-chain antibody to SPIOs using the same protocol.

The skilled person will understand that any label useful in an X-Ray imaging method could be incorporated in the probe. As a non-limiting example of the method, a paramagnetic label could be coupled to a probe targeted to activated platelets. Upon administration of the probe, the paramagnetic label would localize at the site of a clot, embolus or unstable atherosclerotic plaque that could then be visualised by a magnetic resonance imaging technique.

Alternatively, the probe could be radiolabelled (for example with technetium-99m, rubidium-82, thallium 201, F-18, gallium-67, or indium-111), with the activated platelets being visualized using a gamma camera. Also the labelling of activated platelets using computer tomography and ultrasonic methods (e.g. targeting of micro bubbles) is contemplated to be useful with the described antibody.

Applicant discloses herein the use of a probe that targets activated platelets and allows quantification of contrast binding using MRI in an in vivo setting. In one form of the invention a single chain antibody that recognizes only the active conformation of GpIIb/IIIa is used, the antibody being coupled to micro-meter sized paramagnetic iron oxide particles. Intravascular structures are accessible to micron-sized particles that are several orders of magnitude larger than the iron oxide nanoparticles typically used in the art. To the best of the Applicant's knowledge, functional imaging of activated platelets using single-chain antibodies is described herein for the first time.

To demonstrate the use of labeled probes targeted to activate platelets in an in vivo setting, the femoral wire injury model in mice was used (Roque, M., et al., Mouse model of femoral artery denudation injury associated with the rapid accumulation of adhesion molecules on the luminal surface and recruitment of neutrophils. Arterioscler Thromb Vasc Biol, 2000. 20(2): p. 335-42), which leads to a monolayer of platelets 24 hours after injury. The time course of cellular events following femoral wire injury in the mouse is well described and, as demonstrated in FIG. 15C, consistently shows confluent platelet deposition on the denuded endothelium after 24 hours. This was used as the basis for targeting activated platelets with single-chain antibodies against ligand-induced binding sites on the activated GP IIb/IIIa receptor. This antibody confers functional specificity since its binding is dependent upon the presence of fibrinogen or its analogues. These properties make this antibody attractive as a ligand for MPIOs to mediate imaging of platelet thrombus. Using 11.7 T MRI and T2*-weighted MRI, signal void at the areas of strong bead binding was detected. The histologically confirmed quantity of MPIOs bound to the vessel wall correlated significantly to the extent of signal extinction caused by the MPIOs in $T_2^*$ weighted MRI. This MRI method possesses sufficient resolution for imaging small vessels of only 200 μm diameter. The MPIO-induced signal void was sufficiently sensitive to detect signal void even extending the intrinsic negative contrast caused by the arterial vessel wall in $T_2^*$-weighted MRI.

Previous targeted contrast agent approaches have included integrin-conjugated gadolinium rich perfluorocarbon nanoparticles, peptide conjugated nanoparticles of iron oxide, and fibrin specific cyclic peptide labelled with gadolinium. However, the quantity of contrast agent that can be delivered, and therefore the intensity of contrast effect achieved is relatively limited, particularly for low-abundance targets.

Applicants have found that MPIOs carry a high payload of contrast that is not readily dispersed and that is conspicuous on MRI and propose the use of MPIOs for molecular imaging. The versatility of this approach allows generic endovascular imaging of vascular receptors even for different receptor conformations. Sparse epitopes can be efficiently targeted by MPIOs despite their size compared to the ligand itself as demonstrated herein, simultaneously the high iron payload would allow detection of even individual beads and therefore individual receptors depending upon the MPIO-size. Furthermore, the phage display methods described herein offer the possibility of constructing selective ligands to sparse or functional epitopes, therefore allowing deep insights into pathophysiological processes in various diseases. Other important issues are the minimal immunogenicity of single chain antibodies as they only consist of the variable regions, and the size which facilitates the access to clandestine epitopes.

It will be understood that the probes described herein may be used in methods for imaging a blood vessel abnormality in a subject by detection of an activated platelet in a blood vessel. In one form of the method, the detection includes the use of a probe as described herein. It is contemplated that probes the probes are useful with X-ray and CT apparatus found in a standard cardiac catheterization laboratory. The 64-slice CT or the 128-slice CT is proposed to be suitable for the imaging methods described herein. The probes are also proposed to be useful in the context of near-infrared spectrometric imaging (thermography) by using a catheter to introduce the probe.

Abnormalities that may be detected include a ruptured atherosclerotic plaque or an atherosclerotic plaque that is prone to rupture, a thrombus, an embolus, and an accumulation of activated platelets.

The invention will now be further described by reference to the following non-limiting examples.

EXAMPLES

Example 1

Generation of the Single-Chain Antibody $scFv_{anti-LIBS}$ and the Fusion Construct $scFv_{anti-LIBS}$-TAP The generation of the hybridoma cell line expressing a monoclonal antibody against a LIBS epitope on GPIIb/IIIa and its functional characterisation has been described earlier (Schwarz et al. JPET 2004; 308: 1002). Briefly, GPIIb/IIIa purified and eluted with RGD peptides was used as immunogen for hybridoma production. Clones were screened with activated platelets as well as with immobilized GPIIb/IIIa saturated with RGD peptides. One of these clones, monoclonal antibody (mAb) clone 145 demonstrated increased binding to ADP-activated platelets and to platelets pre-incubated with RGD peptides (GRGDSP, BIOMOL Research Laboratories, Plymouth Meeting, Pa.), eptifibatide (Integrilin®, Essex Pharma, Muenchen, Germany), tirofiban (Aggrastat®, MSD, Whitehouse Station, N.J.), and abciximab (ReoPro®, Eli Lilly & Co, Indianapolis, Ind.). The hybridoma was maintained in RPMI, 10% fetal calf serum, 1 mM sodium pyruvat, 10 μM mercaptoethanol, 100 units/ml penicillin, 100 g/ml streptomycin (all from Gibco), and 1×HAT supplement (H0262, Sigma). The $IgG_{anti-LIBS}$ mAb was prepared by affinity purification of hybridoma supernatant using ImmunoPure® IgG Protein G purification (Pierce, Rockford, Ill., USA).

For single-chain antibody cloning, cDNA of the hybridoma was prepared using mRNA purification columns (oligo-dT) and M-MuLV (both Amersham-Pharmacia, Freiburg, Germany). Amplification of the antibody variable regions was achieved by polymerase chain reaction (PCR) using Pfu® Polymerase (Strategene, La Jolla, Calif., USA). The following primers based on sequences from conserved regions of the variable regions of the heavy ($V_H$) and light chain ($V_L$) (Welschof et al. J Immunol Methods 1995; 179: 203) were used: $V_H$ sense: 5'-CCG GCC ATG GCG CAG GTG CAG CTG CAG CAG-3' (SEQ ID NO: 3), $V_H$ antisense: 5'-CC AGG GGC CAG TGG ATA GAC AAG CTT GGG TGT CGT TTT-3' (SEQ ID NO: 4), $V_L$ sense: 5'-AA TTT TCA GAA GCA CGC GTA GAT ATC $^G/_T$TG $^A/_C$T$^G/_C$ ACC CAA $^T/_A$CT CC (SEQ ID NO: 5), $V_L$ antisense: 5'-GAA GAT GGA TCC AGC GGC CGC AGC ATC AGC-3' (SEQ ID NO: 6). The PCR constructs were cloned into the pHOG21 vector system (Kipriyanov et al. J Immunol Methods. 1997; 200: 69, Schwarz et al. FASEB J 2004:18:1704) using the restriction sites Nco I and Hind III for $V_H$ and the restriction sites Mlu I and Not I for $V_L$. The resulting single-chain antibody was termed $scFv_{anti-LIBS}$-TAP has been cloned previously (Hagemeyer et al. Thromb Haemost. 2004; 92: 47) and was transferred to pHOG21 that already included $scFv_{anti-LIBS}$ using the restriction sites Not I and Xba I, thereby creating $scFv_{anti-LIBS}$-TAP (FIG. 1; SEQ ID NO: 1; SEQ ID NO: 2). As a control without binding function of the scFv part, a non-targeted mut-scFv-TAP was generated that contains a single-chain antibody, which originally bound to GP IIb/IIIa, but its heavy-chain CDR3 (complexity determining region) was mutated (RND to AND) and thereby its binding property was lost. All construct were sequenced (FIG. 1).

Example 2

Expression and Purification of scFv Constructs in *E. coli*

*E. coli* (TG1) cells were transformed with the pHOG21 plasmids described above and individual colonies from a freshly streaked agar plate were grown in LB media containing 100 μg/mL ampicillin and 100 mM glucose at 37° C. in 500 mL flasks. Cultures were shaken at 200 rpm for approximate 4-6 hours until an OD (600 nm) of 0.8 was reached. Bacteria were pelleted by centrifugation at 5000 rpm for 10 min at 4° C. and resuspended with LB media containing 100 m/mL ampicillin and 0.4 M sucrose. IPTG was added to a final concentration of 0.25 mM for induction of scFv production and incubated at room temperature (22-24° C.) with 200 rpm for 16-20 hours. For purification of soluble protein from whole cell extract, bacteria were harvested by centrifugation at 5000 rpm for 10 min at 4° C. Pelleted bacteria were resuspended in 5 mL 1× BugBuster® (Novagen, Madison, USA) solution/g pellet and incubated for 15 min at room temperature with gentle shaking. After an additional centrifugation step at 15 000 rpm for 20 min at 4° C., the supernatant containing soluble protein was kept on ice and a protease inhibitor (Complete® Roche, Basel, Switzerland) diluted 1:50 was added. The supernatant containing soluble protein extract was mixed with 500 μL $Ni^{2+}$-Agarose (QIAGEN, Hilden, Germany) and incubated for 1 hour at 4° C. with constant shaking at 150 rpm. $Ni^{2+}$-Agarose, now binding His(6)-tagged proteins, was allowed to settle for 30 min before washed with buffer (50 mM $NaH_2PO_4$, 300 mM NaCl, 20 mM imidazole, pH 8). This batch washing procedure was repeated twice. Finally, scFv fusion proteins were eluted at high imidazole concentrations (250 mM) and subsequently analyzed by gradient SDS-PAGE and Western blotting under reducing conditions. Proteins were transferred onto an Immobilon P membrane (Millipore Corporation, Bedford, USA) for immunoblotting. After blocking the membrane overnight with phosphate buffered saline containing 0.2% Tween20 (PBS-Tween) and 1% BSA, a HRP-labeled anti-His(6)-antibody (Roche, Mannheim, Germany) was added (dilution 1:500) and incubated for 2 hours at room temperature. The membrane was washed several times with PBS-Tween buffer before visualization of peroxidase activity by addition of SuperSignal® Chemiluminescent Substrate (Pierce, Rockford, USA) on a ChemiDoc XRS® (BioRad, Regents Park, NSW, Australia). As a size marker and His(6)-tag positive control a 6×His protein Ladder® (QIAGEN) was used.

Example 3

In Vitro Functional Characterization of the scFv Anti-LIBS-TAP

Blood Preparation

Human blood was collected by venipuncture with a 21-gauge butterfly needle from healthy volunteers and anticoagulated with citric acid. Platelet-rich plasma was obtained by centrifugation (GS-6R centrifuge, Beckmann Coulter, Gladesville, NSW, Australia) at 100×g in plastic tubes at room temperature for 10 min in a centrifuge.

Mouse Blood was collected by intracardial puncture with a 27-gauge needle from C57BL/6 mice and anticoagulated with unfractionated heparin (20 U/mL). A volume of 50 μl was resuspended with 1 mL modified Tyrode's buffer (150 mM NaCl, 2.5 mM KCl, 1.2 mM $NaHCO_3$, 2 mM $MgCl_2$, 2 mM $CaCl_2$, 0.1% BSA, 0.1% Glucose) and centrifuged at 1300×g for 5 min. The supernatant was discarded and the pellet was resuspended with 1 mL modified Tyrode's buffer.
Flow Cytometry Human citrated whole blood was diluted 1/50 in modified Tyrode's buffer, either activated by addition of 20 μM ADP or non-activated and then preincubated for 10 min with 10 μg/mL $IgG_{anti-LIBS}$, $scFv_{anti-LIBS}$, and $scFv_{anti-LIBS}$-TAP. ScFvs were detected by a secondary antibody (Penta His Alexa Fluor 488 Conjugat®, QIAGEN) directed against the Histidin(6)-tag of the scFv. The $IgG_{anti-LiBS}$ was detected by a DTAF-conjugated goat anti-mouse IgG+IgM (H+ L) (Jackson Immuno Research, West Grove, Pa., USA)

Mouse platelets were either activated by addition of 0.1 U/mL Thrombin (Enzyme Research Laboratories, South Bend, 1N, USA) or not activated, and then incubated for 10 min with 10 μg/mL $IgG_{anti-LIBS}$, $SCFV_{anti-LIBS}$, and $scFv_{anti-LIBS}$-TAP. Fluorescence detection was performed as described above. Samples were measured in a FACSCalibur® flow cytometer (Becton Dickinson, San Jose, Calif., USA), after fixation with CellFIX® (Becton Dickinson).

Example 4

Anti-Factor Xa Activity Assay

Inhibition of fXa was determined by the degradation of the chromogenic substrate spectrozyme fXa #222 (American Diagnostica Inc., Greenwich, Conn., USA). Probes were dialyzed against modified Tyrode's buffer (150 mM NaCl, 2.5 mM KCl, 12 mM $NaHCO_3$, 2 mM $MgCl_2$, 2 mM $CaCl_2$, pH 7.4) and adjusted to get 100 nM of $scFv_{anti-LIBS}$, $SCFV_{anti-LIBS}$-TAP and non-targeted mut-scFv-TAP, or free recombinant TAP in a final volume of 165 μl. After adding 10 μl 0.1% human albumin, probes were mixed with 10 μL of 500 μM fXa (Haemochrom, Enzyme Research Laboratories) and compared to fXa alone as positive control. After incubation at room temperature for 10 min, 15 μL chromogenic substrate solution (5 mM) was added and plates were incubated for 15 minutes at room temperature. Finally, reaction was terminated by adding 50 μl stop-solution and absorption was measured at 405 nm in an ELISA reader (Victor$^3$®, Perkin Elmer, Melbourne, Australia).

Example 5

In Vivo Functional Evaluation of Antithrombotic Efficacy and Protection from Bleeding in a Mouse Model C57BL/6 mice with weights 22-38 g (Charles River Laboratories, Wilmington, Mass., USA) were used for the present study. Care and use of laboratory animals followed the national guidelines and was approved by the institutional animal care and ethics committee at the University of Freiburg and at the Baker Heart Research Institute. Mice were anesthetized with Isoflurane using a exicator for a few seconds and i.p. injection with Ketamin (Ketanest® 100 mg/kg BW) and Xylazin (Rompun® 5 mg/kg BW) and placed under a dissecting microscope. After absence of any reflexes, an incision of the skin was made directly on the top of the right common carotid artery region. The fascia was bluntly dissected and a segment of the right common carotid artery was exposed. Then a nano doppler flow probe (Model 0.5 VB, Transonic Systems, Ithaca, N.Y., USA) was positioned over the artery and the carotid blood flow was measured by a flow meter (model T106, Transonic Systems, Ithaca, N.Y., USA). Thrombosis was induced by applying a piece of filter paper (1×2 mm) (Gel Blot Paper, GB003, Schleicher and Schuell, Keene, N.H., USA) saturated with ferric chloride (10% solution) (Sigma, St. Louis, Mo., USA) under the right carotid artery and removed after 3 min. Thrombotic occlusion was considered to occur when flow decreased to 0.0±0.2 mL/min, a range corresponding to the accuracy of the system as specified by the manufacturer.

One minute prior the ferric chloride treatment, mice were infused through the tail vein with saline (negative control) (0.9% sodium chloride) 100 μl, enoxaparin (positive control) (Clexane® Sanofi Aventis, Paris, France) with 1 mg/kg BW diluted with saline to volume of 100 μl, and with various doses of purified recombinant scFv$_{anti\text{-}LIBS}$-TAP, scFv$_{anti\text{-}LIBS}$, non-targeted mut-scFv-TAP, and rTAP. All doses of used scFvs and rTAP were dissolved to a volume of 100 μl. To ensure that all drugs were infused in mice the aditus was flushed with 100 μl saline.

Mouse bleeding time was measured as described previously by Xinkang. The anesthetized mice were placed under the dissecting microscope. About 1-2 mm from the tip of the mouse tail (in about 1 mm diameter) a cut was made with a disposable surgical blade. The time at which the tail first stopped bleeding for more than 30 sec was recorded in seconds.

Statistical Analysis

Data are presented as mean±standard deviations for the indicated number (N) of mice. The statistical comparisons were made by analysis of variance (ANOVA following a Newmann-Keuls-test) and differences were considered to be significant at $p<0.05$.

Example 6

Use of Labelled Single-Chain Antibodies for Diagnostic Imaging

Figure 9:
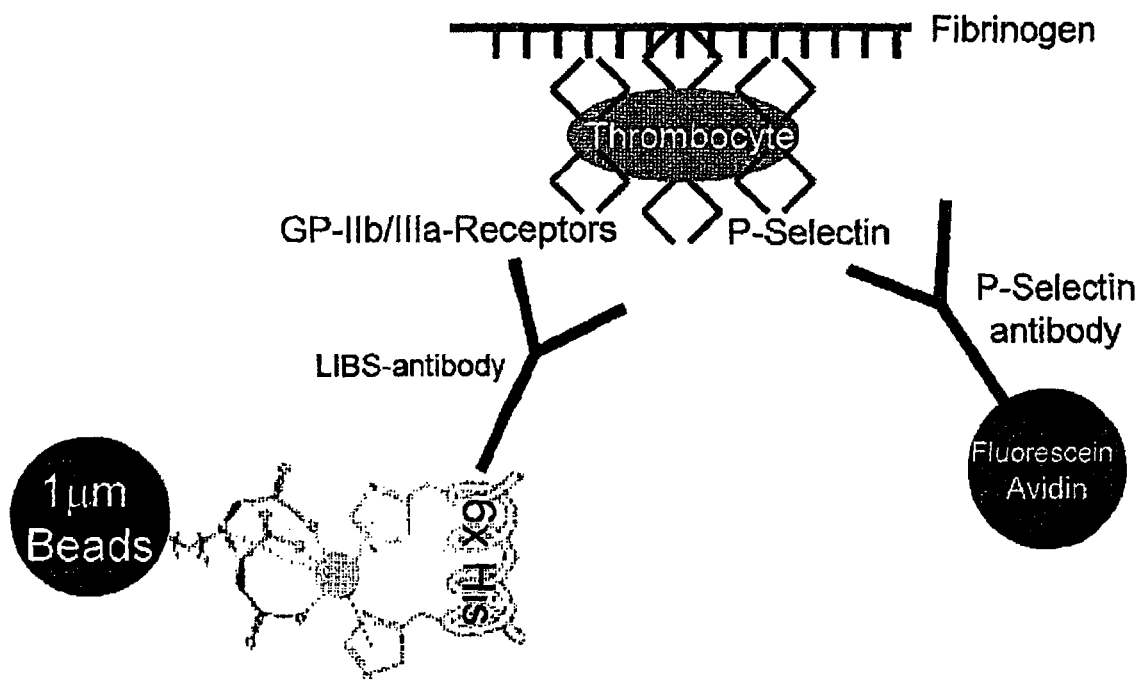
FIG. 9 shows an overview of the thrombus adhesion assay. Platelets immobilized on fibrinogen were targeted with the anti-LIBS bead contrast agent via the activated GP IIb/IIIa receptor. Co-staining of platelets was performed using P-selectin antibodies and fluorescein-avidin in order to demonstrate selective binding of the contrast agent to platelets only.

The single-chain antibody anti-LIBS as described in Example 1 were mixed with Superparamagnetic Iron Oxide particles (SPIOs) that were functionalized to interact with proteins that include a His-tag (Dynabeads® TALON™; Dynal Biotech). Other methods (e.g. chemical coupling) to couple antibodies to paramagnetic beads can also be used. Binding of the contrast agent to activated platelets (which are a major and essential constituent of thrombi and emboli) was demonstrated by an adhesion assay. The activation of platelets used in the assay was monitored by fluorescence microscopy demonstrating the upregulation of P-selectin expression on the platelet surface as well as with fluorescence detection of an increase in intracellular $Ca^{2+}$ level. The assay involved the immobilization of activated platelets on a fibrinogen-covered cover slip by incubating the platelets for 30 minutes at 37° C. After washing of the cover slips, the fibrinogen-platelet matrix was exposed to the contrast agent for 30 minutes. In order to exclude unspecific binding and to demonstrate binding of the contrast agent to platelets only, a co-staining of platelets was performed using P-selectin antibodies and secondary staining with fluorescein-avidin (FIG. 9). Using confocal microscopy, binding of the red-appearing auto-fluorescent contrast agent to platelets was demonstrated by simultaneous green fluorescence of the P-selectin-stained platelets. A 3D-reconstruction using the z-stack from confocal microscopy is shown in FIG. 10.

Figure 11:
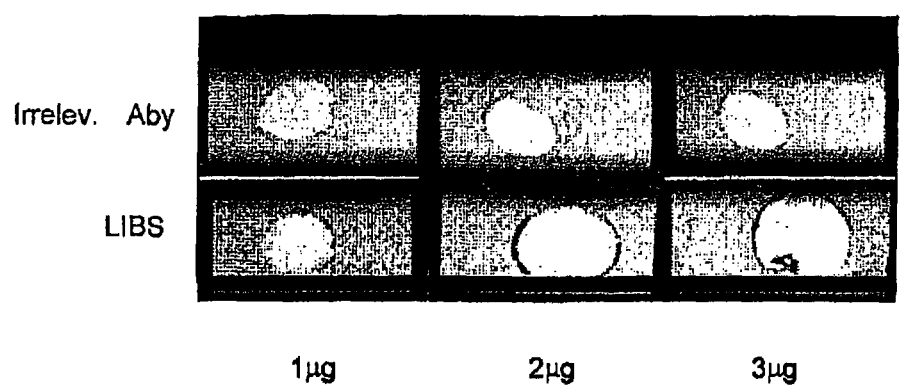
FIG. 11 shows an MRI of human thrombi, 3D FLASH-images reconstructed perpendicular to the longitudinal axes. Thrombi exposed to different concentrations of anti-LIBS bead contrast agent show negative contrast as caused by SPIO beads in T2" (black ring around the thrombus). Thrombi exposed to irrelevant antibodies on beads do not show this negative contrast.
Figure 12:
FIG. 12 shows immunohistochemistry of platelets using mouse anti-human P-selectin and Nova Red (brown). The anti-LIBS bead contrast agent appears yellow and is only present in the areas of platelet aggregates on the thrombus surface.

Furthermore, to assess the suitability of the imaging method in vitro, magnetic resonance experiments were performed to show binding of single-chain antibody to activated platelets on thrombus surfaces. For these experiments, human thrombi were generated artificially by adding actin, adenosine diphosphate and calcium chloride to human platelet rich plasma and incubating the mixture for 15-30 minutes at 37° C. Thrombi were exposed to different concentrations of the contrast agent and incubated for another 30 minutes at 37° C. Finally, the thrombi were washed twice in PBS buffer and fixed with 4% paraformaldehyde. After 4 hours of fixation, the thrombi were embedded into wells of a 24-well cell-culture plate, surrounded by gadolinium-spiked 2% agarose. Magnetic Resonance Imaging (MRI) was performed on a 3 Tesla clinical scanner, employing the standard wrist coil. A 3D FLASH sequence with TE/TR 9.3 ms/700 ms was run with a resolution of 130×130×200 μm and images were reconstructed perpendicular to the longitudinal axes of the clots in an overnight run. Negative contrast, as caused by SPIO in $T2^*$-weighted MRI, was observed as a black ring around the thrombi incubated with the LIBS-targeted antibody in a dose-dependent manner (FIG. 11). Furthermore, bead binding was confirmed using immunohistochemistry with an anti-P-selectin antibody and staining with NovaRed in paraffin-embedded sections: FIG. 4 shows conglomerates of platelets (brown) with binding of beads (yellow) to areas with platelets. These results indicate successful binding of the designed contrast agent to activated platelets in vitro, which can be detected with clinically relevant field strengths by MRI.

Example 7

Use of Labelled Single-Chain Antibodies for Diagnostic Imaging in a Mouse Model

Single-Chain Antibody Generation and Conjugation to 1 μm Iron Oxide Microparticles The LIBS epitope on GPIIb/IIIa represents an abundant and highly specific target for activated platelets. The mAb anti-LIBS 145 binds to GPIIb/IIIa only in its active conformation and it demonstrates strong binding to ADP-activated platelets in the presence of fibrinogen (Schwarz JPET 2004). The mAb anti-LIBS 145 expressing hybridoma cell line was used as the basis for the cloning of an anti-LIBS single-chain antibody (scFv). mRNA of this hybridoma cell line was prepared and reverse transcribed using an oligo-dT primer. The variable regions of the antibody's heavy and light chain were amplified by PCR using primers that anneal to conserved regions at the 5' and 3' ends of the variable regions. The PCR products were cloned into the pHOG21 vector, TG1 E. coli were transformed, and individual clones were assessed for LIBS-typical binding to GPIIb/IIIa was tested in flow cytometry with activated platelets. Finally the best binding scFv$_{LIBS}$ was produced in LB media containing 100 μg/mL ampicillin and 100 mM glucose at 37° C. in 500 mL flasks. Cultures were shaken at 200 rpm for approximate 4-6 hours until an OD (600 nm) of ~0.8 was reached. Bacteria were pelleted by centrifugation at 5000 rpm for 10 min at 4° C. and resuspended with LB media containing 100 μg/ml ampicillin and 0.4 M sucrose. IPTG was added to a final concentration of 0.25 mM for induction of scFv production and incubated at room temperature (22-24° C.) with 200 rpm for 16-20 hours. Bacteria were harvested by centrifugation at 5000 rpm for 10 min at 4° C., the pelleted bacteria were resuspended in 5 mL 1×BugBuster®(Novagen) solution/g pellet and incubated for 15 min at room temperature with gentle shaking. After an additional centrifugation step at 15 000 rpm for 20 min at 4° C., the supernatant containing soluble protein was kept on ice and a protease inhibitor (Complete® Roche) diluted 1:50 was added. The supernatant was mixed with 500 µL $Ni^{2+}$-Agarose (Qiagen) and incubated for 1 hour at 4° C. with constant shaking at 150 rpm. $Ni^{2+}$-Agarose, now binding His(6)-tagged proteins, was allowed to settle for 30 min before washed with buffer (50 mM $NaH_2PO_4$, 300 mM NaCl, 20 mM imidazole, pH 8). This batch washing procedure was repeated twice. Finally, the scFv was eluted at high imidazole concentrations (250 mM) and dialyzed. Functionality of the scFv preparations were evaluated in flow cytometry.

Autofluorescent cobalt-functionalized MPIOs (1 µm) were conjugated to the histidine-tag of the LIBS single-chain antibody referring to the protocol of the manufacturer (Dyna) Biotech, Oslo, Norway). In brief, after washing 1 mg of beads was incubated with the LIBS antibody for 10 min at room temperature (RT) to bind approximately 10 µg of histidine-tagged antibody. The tube containing the suspension was then placed on a magnet until the beads had migrated to the side of the tube and the supernatant discarded. This washing was repeated four times using a binding and washing buffer containing 50 mM NaP (pH 8), 300 mM NaCl and 0.01% Tween-20.

LIBS-MPIO Binding to Activated Platelets

An adhesion assay was performed to demonstrate binding of the LIBS-M PIO to activated platelets. Blood from a healthy volunteer taking no medication was anticoagulated with citric acid and centrifuged at 1000 rpm for 10 min. The resulting platelet rich plasma was diluted with PBS (1:10) and 100 µl added onto fibrinogen-covered cover slips, which had been preincubated with 20 µg/ml fibrinogen for 1 hour at 38° C. and blocked with 1% BSA for 1 hour at room temperature. After 30 min incubation at 38° C., cover-slips were washed with PBS and under continuous rotation either incubated with 0.5 µg of LIBS-MPIO (LIBS-MPIO) or an equivalent conjugated irrelevant single-chain antibody control (Control-MPIO) for another 30 min at 38° C. Cover-slips were then washed twice for 5 min with PBS and blocked with 10% goat-serum (Vector, Burlingame, Calif./USA) for 1 hour at RT. To demonstrate specific binding of the contrast agent, platelets were co-stained for P-selectin using a monoclonal mouse anti-human CD62 antibody (1:100, R&D Systems, Abingdon, UK) with a biotinylated goat anti-mouse IgG (Vector, Burlingame, Calif./USA) serving as secondary antibody. Finally, 1:200 diluted Fluorescin Avidin D (Vector, Burlingame, Calif./USA) was added and incubated for 1 hour and RT. Cover-slips were fixed using CellFix (BD Biosciences, Heidelberg, Germany) and evaluated by confocal microscopy.

Mice

Wire injury was performed in male C57BL/6 mice weeks (Jackson Laboratories, UK), mean age of 10±0.8 weeks. Mice received water and standard chow diet ad libitum. All procedures were performed in accordance with the UK Home Office Animals (Scientific Procedures) Act 1986.

Femoral Wire Injury, Bead Perfusion and Sample Preparation

Single-sided femoral wire injury was performed under general anesthesia, using a combination of Hypnorm (25 mg/kg, Bayer, Germany) and Hypnoval (25 mg/kg, Bayer, Germany) administered subcutaneously, as described previously (Roque, M., et al., *Mouse model of femoral artery denudation injury associated with the rapid accumulation of adhesion molecules on the luminal surface and recruitment of neutrophils*. Arterioscler Thromb Vasc Biol, 2000. 20(2): p. 335-42). Under a surgical microscope, a groin incision was made. The femoral artery was exposed, and an arteriotomy was made distal to the epigastric branch using 30G injection cannula (BD, Erembodegem, Belgium). A 0.010" guidewire (Boston Scientific, Natick, USA) was inserted, advanced to the aortic bifurcation and pulled back. After removal of the wire, the arteriotomy site was ligated and the skin closed using silk sutures. After 24 hours, mice were terminally anesthetized by inhalation of isoflurane. The chest was opened by thoracotomy, the heart exposed and the right atrium cut. A 30G needle was inserted through the apex of the left ventricle and the animal perfused with 10 ml of PBS to eliminate the blood. Perfusion was continued with 5 mL PBS containing either LIBS-MPIO or control-MPIO ($1.5 \times 10^8$ beads/ml for each). After 30 minutes, mice were again perfused under physiological pressure with 10 mL PBS followed by 5 mL 4% Paraformaldehyde (PFA) containing 2 mM gadoteridiol (Prohance, Bracco, UK). The skin was removed, the leg with the area of injury cut, kept in 4% PFA/2 mM gadoteridiol for 24 hours and then embedded in a glass MR tube containing 2% high-grade, with low melting point agarose. (Cambrex, Rockland, Me./USA).

Ex Vivo MRI

Ex vivo MRI was performed at 11.7 T using a 13 mm $^1$H birdcage radiofrequency coil (RAPID Biomedical, Würzburg, Germany). A 3D gradient echo sequence (TE=4 ms/TR=90 ms, field of view 13×13×19.5 mm, matrix size 256×256×384, two averages, imaging time ~7 h per sequence) was used in an unattended overnight run. Data reconstruction was performed off-line with a final isotropic resolution of 25 µm$^3$.

Histology and Quantification of MPIO Binding in the Injured Femoral Artery

After MRI, specimens were decalcified in 10% Formic Acid overnight, dehydrated through graded ethanol solutions and Neo-clear (VMR, UK), paraffin embedded and serially sectioned (8 µm thick). Specimens were stained for iron (Accustain, Sigma, Germany) referring to the manufacturers protocol. The number of conjugated MPIOs bound to the injured luminal vessel wall was quantified and averaged in 20-25 sections per animal from the injured vessel site using light microscopy.

For platelet visualization with immunhistochemistry, deparaffinized and rehydrated sections were saturated in 1% $H_2O_2$ for 20 min, added to simmering citrate buffer and boiled for 4 min in a pressure cooker for antigen retrieval. Specimens were washed in PBS Tween, incubated with protein block solution (DakoCytomation, Hamburg, Germany) for 4 hours, and incubated overnight at 4° C. with rat anti-mouse CD61 antibody (1:8000, InterCell Technologies, FI/USA). After washing with PBS, biotinylated goat anti-hamster IgG (1:200, Vector, Burlingame, Calif./USA) secondary antibody. Slides were washed with PBS, and peroxidase reaction was performed using Vectastain RTU Elite ABC-reagent and Vector NovaRed (both Vector, Burlingame, Calif./USA). Finally, sections were deyhdrated, mounted with Permount (Biomeda, Foster City, Calif./USA) and bead binding to platelets was evaluated on a light microscope.

MPIO Binding in the Femoral Artery by Ex Vivo MRI

Quantification of the MPIO binding was performed blinded. Antibody-conjugated MPIO binding was defined as a clear circular signal void on the luminal surface of the femoral artery in ≥2 consecutive slices. MPIOs appearing in multiple sections were counted only once. Segmented images were reconstructed in three dimensions using the 3D Constructor plug-in for ImagePro Plus to visualize the distribution of MPIO binding throughout the femoral artery.

Statistical Methods

Data are expressed as mean±standard deviation. Parametric data were compared using t-tests. Statistical significance was assigned to P<0.05.

Results

LIBS-MPIO Detects Activated Glycoprotein IIb/IIIa Receptors on Platelets

Figures 13A, 13B, 13C:
FIG. 13A to FIG. 13C show immunfluorescence of fibrinogen-fixed human platelets stained for avidin-fluorescein using a CD62P antibody. (A) Platelets incubated with the red autofluorescing LIBS-MPIO contrast agent show specific binding to platelets represented by the green avidin-fluorescein induced signal, whereas incubation of platelets with Control-MPIO contrast agent shows no binding (B). (C) represents a 3D reconstruction of a z-stack from platelets incubated with LIBS-MPIO and stained for P-selectin, demonstrating the principle of targeting LIBS on activated GP IIb/IIIa receptors.

In FIG. 13, human platelet thrombi labeled with anti-P-selectin antibody fluorescence bright green. Superimposed on the platelet thrombi are red areas corresponding to autofluorescent LIBS-M PIO (Panel A). The MPIOs are confined to the platelet thrombi without non-specific background retention. By contrast, in Panel B, there is complete absence of binding of control-MPIO conjugated to an irrelevant single chain antibody. A 3D z-stack reconstruction in confocal microscopy shows LIBS-MPIO binding (red) to P-selectin-stained platelets (green), emphasizing their relative size and spatial relations.

LIBS-MPIO Bound to Wall-Adherent Platelets Detected by Ex Vivo MRI

Unilateral femoral artery wire-injury was performed in 13 mice without complication. Seven mice were perfused with LIBS-MPIO and 6 with control-MPIO via the left ventricle. One control animal was excluded from the quantification analysis, of marked variation in the quantification of MPIOs between two observers.

Figure 14A:
FIG. 14A and FIG. 14B show 11.7 T ex vivo MRI, 3D gradient echo sequence (TE=4 ms/TR=90 ms, field of view 13×13×19.5 mm, matrix size 256×256×384), isotropic resolution of 25 $\mu m^3$. (A) shows the injured femoral artery in a LIBS-MPIO perfused mouse. Black intrinsic vessel-wall signal can be observed in the LIBS-MPIO mouse as well as in the Control-MPIO mouse (B), but attached to the luminal side of the femoral artery signal void can be observed as an indicator for MPIO-binding in the LIBS-MPIO mouse (A, arrows). Quantification of MPIO-induced MRI signal-void reveals a significant difference between LIBS-MPIO and Control-MPIO perfused mice ($p<0.05$).
Figure 14B:

Ex vivo T2*-weighted MRI of injured arterial segment often demonstrated intrinsic low signal areas within the arterial wall (FIG. 14B). Distinct from this was the appearance of circular signal voids within the vessel lumen but adjacent to the vessel wall. This feature was observed in the wire-injured arteries of all mice injected with LIBS-MPIO (FIG. 14A). In quantitative analysis luminal areas of low signal suggesting MPIO-accumulation were significantly higher in LIBS-MPIO injected animals than in control-MPIO perfused animals (23.72 vs. 6.2; P<0.01, FIG. 14C).

Figures 15A, 15B, 15C:
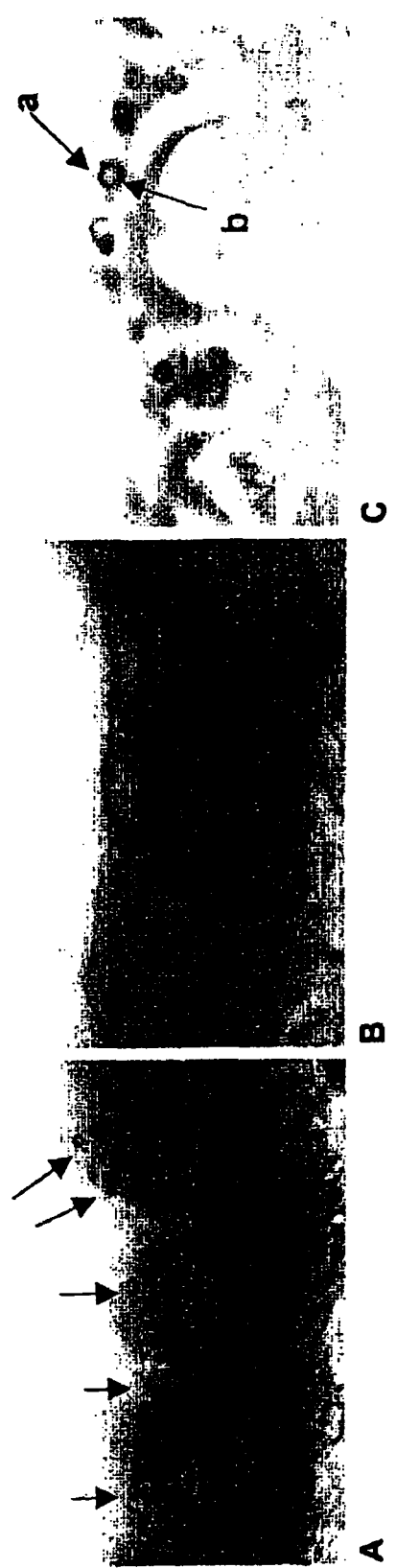

MPIO binding was confirmed in histology (FIG. 15), with significantly higher MPIO-binding in LIBS-MPIO injected animals (9.98 vs. 0.5 beads per section, P<0.01; FIG. 15D). Colocalization of MPIOs and platelet adhenerce to the arterial wall was confirmed by immunohistochemistry. In FIG. 15C, MPIOs are demonstrated to be present in association with positive immunostaining for the platelet marker CD61.

Figure 16:
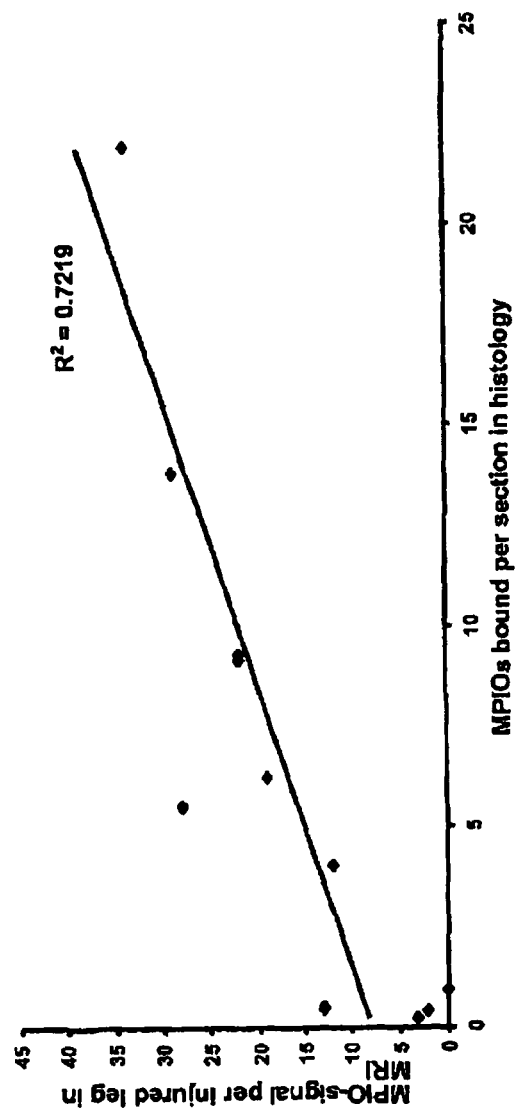
FIG. 16 shows a correlation analysis between MPIO-signal per injured leg in MRI and MPIOs bound per section in histology, showing a significant correlation ($R^2=0.72$)

An analysis of bead quantification in histology compared to quantification by ex vivo MRI revealed a strong correlation ($R^2=0.7219$, P<0.001; FIG. 16). Therefore, MPIO signal quantity determined by MRI directly reflected the quantity of MPIOs bound to the injured vessel wall.

Finally, it is to be understood that various other modifications and/or alterations may be made without departing from the spirit of the present invention as outlined herein.

The invention claimed is:

1. A single chain antibody that specifically binds to the activated state of the platelet integrin receptor GP IIb/IIIa and that has substantially no effect upon thrombosis when bound to the activated state of said receptor, the single chain antibody comprising (1) a heavy chain variable region that comprises the amino acid sequence of SEQ ID NO: 7, the amino acid sequence of SEQ ID NO: 8 and the amino acid sequence of SEQ ID NO: 9, and (2) a light chain variable region that comprises the amino acid sequence of SEQ ID NO: 10, the amino acid sequence of SEQ ID NO: 11 and the amino acid sequence of SEQ ID NO: 12.

2. The antibody of claim 1, wherein the heavy chain variable region comprises the amino acid sequence beginning at position 36 and ending at position 158 of SEQ ID NO: 2.

3. The antibody of claim 1, wherein the light chain variable region comprises the amino acid sequence beginning at position 168 and ending at position 284 of SEQ ID NO: 2.

4. The antibody of claim 1, further comprising a label.

5. The antibody of claim 4, wherein the label comprises a contrast agent for magnetic resonance imaging.

6. The antibody of claim 4, wherein the label comprises a paramagnetic bead.

7. The antibody of claim 4, wherein the label comprises a superparamagnetic iron oxide particle (SPIO).

8. The antibody of claim 4, wherein the label comprises a micron-sized paramagnetic iron oxide (MPIO).

9. The antibody of claim 4, wherein the label is radioactive or detectable with an X-ray imaging method.

10. The antibody of claim 4, wherein the label is selected from technetium-99m, rubidium-82, thallium 201, F-18, gallium-67, or indium-111.

11. A composition comprising a single chain antibody and a pharmaceutically active element bound thereto, wherein the single chain antibody specifically binds to the activated state of the platelet integrin receptor GP IIb/IIIa and has substantially no effect upon thrombosis when bound to the activated state of said receptor, the single chain antibody comprising (1) a heavy chain variable region that comprises the amino acid sequence of SEQ ID NO: 7, the amino acid sequence of SEQ ID NO: 8 and the amino acid sequence of SEQ ID NO: 9, and (2) a light chain variable region that comprises the amino acid sequence of SEQ ID NO: 10, the amino acid sequence of SEQ ID NO: 11 and the amino acid sequence of SEQ ID NO: 12.

12. The composition of claim 11, wherein the heavy chain variable region comprises the amino acid sequence beginning at position 36 and ending at position 158 of SEQ ID NO: 2.

13. The composition of claim 11, wherein the light chain variable region comprises the amino acid sequence beginning at position 168 and ending at position 284 of SEQ ID NO: 2.

14. The composition of claim 11, wherein the pharmaceutically active element comprises an anticoagulant.

15. The composition of claim 11, wherein the pharmaceutically active element is tick anticoagulant protein (TAP).

16. The composition of claim 11, wherein the pharmaceutically active element is hirudin.

17. An isolated or purified polypeptide comprising the sequence set forth in SEQ ID NO: 2.

* * * * *